United States Patent
Nojiri et al.

(10) Patent No.: US 10,071,028 B2
(45) Date of Patent: *Sep. 11, 2018

(54) DENTAL ADHESIVE

(71) Applicant: KURARAY NORITAKE DENTAL INC., Kurashiki-shi (JP)

(72) Inventors: Yamato Nojiri, Tainai (JP); Mitsuru Takei, Yokohama (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/315,497

(22) PCT Filed: Jun. 10, 2015

(86) PCT No.: PCT/JP2015/002914
§ 371 (c)(1),
(2) Date: Dec. 1, 2016

(87) PCT Pub. No.: WO2015/190099
PCT Pub. Date: Dec. 17, 2015

(65) Prior Publication Data
US 2017/0196778 A1    Jul. 13, 2017

(30) Foreign Application Priority Data

Jun. 10, 2014 (JP) .................. 2014-119595

(51) Int. Cl.
*A61K 6/083* (2006.01)
*C08F 216/12* (2006.01)
(Continued)

(52) U.S. Cl.
CPC ............ *A61K 6/083* (2013.01); *A61K 6/08* (2013.01); *A61K 6/087* (2013.01); *C08F 22/38* (2013.01); *C08F 216/125* (2013.01); *C08F 222/1006* (2013.01); *C08F 222/26* (2013.01); *C08F 22/105* (2013.01); *C08F 22/385* (2013.01); *C08F 30/02* (2013.01); *C08F 220/20* (2013.01);
(Continued)

(58) Field of Classification Search
CPC .......... A61K 6/08; A61K 6/083; A61K 6/087; C08F 22/105; C08F 22/38; C08F 22/385; C08F 30/02; C08F 216/125; C08F 220/20; C08F 216/40; C08F 220/346; C08F 222/1006; C08F 222/26; C08F 2222/1013; C08F 2222/102; C08F 236/14
See application file for complete search history.

(56) References Cited

U.S. PATENT DOCUMENTS

| 4,719,297 A | 1/1988 | Henne et al. |
| 5,300,537 A * | 4/1994 | Muller .......... A61L 24/06 433/228.1 |
| 5,741,543 A * | 4/1998 | Winslow .......... C09J 4/06 427/208.4 |
| 5,744,511 A | 4/1998 | Kazama et al. |

(Continued)

FOREIGN PATENT DOCUMENTS

| EP | 0009348 B1 | 7/1983 |
| JP | 57-197289 A | 12/1982 |

(Continued)

OTHER PUBLICATIONS

Arkema, "GPS Safety Summery: Triethyleneglycol dimethacrylate", Dec. 15, 2014. Published online at https://www.arkema.com/export/shared/.content/media/downloads/socialresponsability/safety-summuries/Photocure-Resins-SR-205-Triethyleneglycol-Dimethacrylate-GPS-2014-12-15-V0.pdf, Accessed on Nov. 6, 2017. (Year: 2014).*

(Continued)

*Primary Examiner* — Ling Siu Choi
*Assistant Examiner* — David L Miller
(74) *Attorney, Agent, or Firm* — Oblon, McClelland, Maier & Neustadt, L.L.P.

(57) ABSTRACT

The present invention provides a dental adhesive exhibiting excellent initial bond strength and bond durability to both enamel and dentin. The present invention relates to a dental adhesive containing: an asymmetric acrylamide-methacrylic acid ester compound (a); an acid group-containing (meth)acrylic polymerizable monomer (b); and a water-soluble polymerizable monomer (c). The asymmetric acrylamide-methacrylic acid ester compound (a) is represented by the following general formula (1):

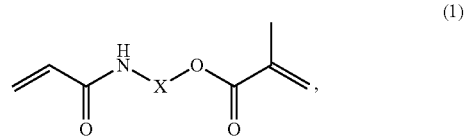

(1)

where X is an optionally substituted, linear or branched $C_1$ to $C_6$ aliphatic group or an optionally substituted aromatic group, the aliphatic group is optionally interrupted by at least one linking group selected from the group consisting of —O—, —S—, —CO—, —CO—O—, —O—CO—, —$NR^1$—, —CO—$NR^1$—, —$NR^1$—CO—, —CO—O—$NR^1$—, —O—CO—$NR^1$—, and —$NR^1$—CO—$NR^1$—, and $R^1$ is a hydrogen atom or an optionally substituted, linear or branched $C_1$ to $C_6$ aliphatic group.

8 Claims, No Drawings

(51) Int. Cl.
    *C08F 222/26*     (2006.01)
    *A61K 6/08*     (2006.01)
    *C08F 222/10*     (2006.01)
    *C08F 22/38*     (2006.01)
    *A61K 6/087*     (2006.01)
    *C08F 220/40*     (2006.01)
    *C08F 220/34*     (2006.01)
    *C08F 236/14*     (2006.01)
    *C08F 220/20*     (2006.01)
    *C08F 30/02*     (2006.01)
    *C08F 22/10*     (2006.01)

(52) U.S. Cl.
    CPC .......... *C08F 220/40* (2013.01); *C08F 236/14* (2013.01); *C08F 2220/346* (2013.01); *C08F 2222/102* (2013.01); *C08F 2222/1013* (2013.01)

(56) References Cited

U.S. PATENT DOCUMENTS 6,953,832 B2     10/2005     Moszner et al.
2005/0009946 A1     1/2005     Oguri et al.
2005/0049326 A1*     3/2005     Park .................. A61K 6/083
    523/118

FOREIGN PATENT DOCUMENTS

| JP | 3-204846 A | 9/1991 |
| JP | 9-3109 A | 1/1997 |
| JP | 10-245525 A | 9/1998 |
| JP | 11-500152 A | 1/1999 |
| JP | 2000-159621 A | 6/2000 |
| JP | 2002-212019 A | 7/2002 |
| JP | 2003-96122 A | 4/2003 |
| JP | 2005186505 A * | 7/2005 |
| JP | 2013-209341 A | 10/2013 |
| WO | 96/24644 A1 | 8/1996 |

OTHER PUBLICATIONS

International Search Report dated Aug. 25, 2015, in PCT/JP2015/002914, filed Jun. 10, 2015.

* cited by examiner

DENTAL ADHESIVE

TECHNICAL FIELD

The present invention relates to a dental adhesive containing an asymmetric acrylamide-methacrylic acid ester compound. Specifically, the present invention relates to a dental adhesive used for bonding between tooth hard tissues (tooth structures) and dental restorative materials such as dental composite resins, dental compomers, and dental resin cements.

BACKGROUND ART

For restoration of tooth structures (enamel, dentin, and cementum) damaged, for example, by dental caries, restorative filling materials such as filling composite resins and filling compomers, or crown restoration materials such as metal alloys, porcelains, and resin materials, are typically used. In general, however, restorative filling materials and crown restoration materials (both of these materials may collectively be referred to as "dental restorative materials" in the present description) themselves have no adhesive properties to tooth structures. This is why bonding between tooth structures and dental restorative materials conventionally employs various adhesive systems involving the use of adhesives. An example of conventionally-employed adhesive systems is an adhesive system of the so-called acid etching-type, in which the surface of a tooth structure is subjected to an etching treatment using an acid etching agent such as an aqueous phosphoric acid solution, and then a bonding material, which is an adhesive, is applied to the tooth structure so as to bond the tooth structure and a dental restorative material.

Adhesive systems of the so-called self-etching type, which involve no use of any acid etching agent, have also been known. Self-etching adhesive systems that had been predominantly used in the past are two-step adhesive systems in which a self-etching primer containing an acidic monomer, a hydrophilic monomer, and water is applied to the surface of a tooth structure and then a bonding material containing a crosslinkable monomer and a polymerization initiator is applied directly to the primer without rinsing with water. In recent years, however, one-step adhesive systems using a one-part dental adhesive (one-part bonding material) having functions of both a self-etching primer and a bonding material have been widely used.

In general, such a one-part bonding material contains monomer components such as an acidic monomer, a hydrophilic monomer, and a crosslinkable monomer, and (meth)acrylate compounds are usually used as such monomer components.

One-part bonding materials are required to have high adhesiveness to tooth structures (in particular, enamel and dentin) and good storage stability, and further improvement of these properties is required. To meet these requirements, the use of a (meth)acrylamide compound, which is a monomer component less susceptible to hydrolysis than a (meth)acrylate compound, has been reported to provide a dental composition with improved storage stability and high adhesiveness to dentin and enamel (see, for example, Patent Literatures 1 and 2).

Patent Literature 1 proposes a one-part dental adhesive composition containing: an acidic monomer; a bifunctional (meth)acrylamide compound represented by the general formula (3) having two (meth)acrylamide groups both of which are secondary amide groups; a (meth)acrylamide compound represented by the general formula (4) having two (meth)acrylamide groups both of which are tertiary amide groups; water; and a curing agent (hereinafter, in the present description, a (meth)acrylamide compound having two (meth)acrylamide groups both of which are secondary amide groups and a (meth)acrylamide compound having two (meth)acrylamide groups both of which are tertiary amide groups may be referred to as symmetric (meth)acrylamide compounds, for the sake of convenience).

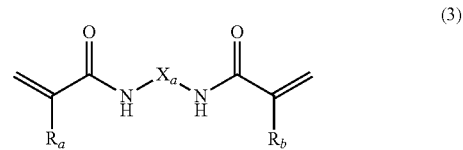

(3)

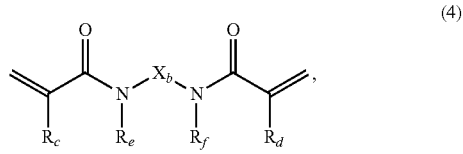

(4)

where $R_a$, $R_b$, $R_c$, and $R_d$ are each independently a hydrogen atom or a methyl group, $R_e$ and $R_f$ are each independently a group other than a hydrogen atom, such as an alkyl group or an aryl group, and $X_a$ and $X_b$ are each independently a divalent organic group optionally having an oxygen atom and a nitrogen atom.

However, most of the bifunctional (meth)acrylamide compounds represented by the general formula (3) have the following disadvantages. These compounds are solid in nature and have poor compatibility with other monomers. Therefore, in a dental composition containing this solid compound, deposition or phase separation of the monomers occurs, or phase separation of the components occurs when air-blowing is performed for use, resulting in low storage stability and poor adhesiveness to tooth structures. Some of the bifunctional (meth)acrylamide compounds represented by the general formula (3) are oily in nature and have good compatibility with other monomers, but a dental composition containing this oily compound has the disadvantage of low adhesiveness to tooth structures. Furthermore, the (meth)acrylamide compounds represented by the general formula (4) are also oily in nature and have good compatibility with other monomers, but a dental composition containing this oily compound has the disadvantage of low adhesiveness to tooth structures.

Patent Literature 2 proposes a dental composition containing: an acidic monomer; an asymmetric bifunctional (meth)acrylamide compound represented by the general formula (5) having two (meth)acrylamide groups, one of which is a secondary amide group and the other of which is a tertiary amide group (hereinafter, in the present description, a (meth)acrylamide compound having two (meth)acrylamide groups, one of which is a secondary amide group and the other of which is a tertiary amide group may be referred to as an asymmetric (meth)acrylamide compound, for the sake of convenience).

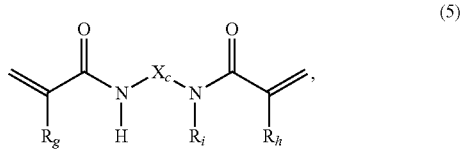

(5)

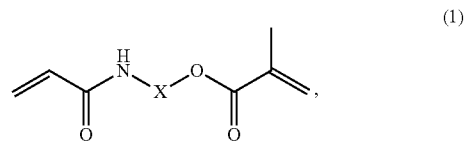

(1)

where $R_g$ and $R_h$ are each independently a hydrogen atom or a methyl group, $R_i$ is an alkyl group other than a hydrogen atom, and $X_c$ is a divalent organic group optionally having an oxygen atom and a nitrogen atom.

The composition disclosed in Patent Literature 2 mentioned above has good storage stability because its components are highly compatible with one another and thus difficult to separate from one another. This composition further has good initial bond strength to both dentin and enamel. This composition, however, has been found to have the disadvantage of low bond durability. Subsequent studies by the present inventors have revealed that this composition still has room for improvement.

Patent Literature 3 proposes an adhesive component containing a carboxamide group-containing (meth)acrylic acid ester and suitable for treatment of collagen-containing materials such as bones and teeth.

The composition disclosed in Patent Literature 3 mentioned above is proposed as an alternative treatment agent to acid etching agents but the etching effect of this composition on tooth structures is not strong enough, and thus has the disadvantage of low adhesiveness to both enamel and dentin.

CITATION LIST

Patent Literature

Patent Literature 1: JP 2002-212019 A
Patent Literature 2: JP 2013-209341 A
Patent Literature 3: JP 03(1991)-204846 A

SUMMARY OF INVENTION

Technical Problem

It is an object of the present invention to provide a dental adhesive that has excellent initial bond strength and bond durability to both enamel and dentin. It is another object of the present invention to provide a dental adhesive that has good storage stability due to low likelihood of separation of the components.

Solution to Problem

The present invention that has solved the above-described problems is a dental adhesive containing:

an asymmetric acrylamide-methacrylic acid ester compound (a);

an acid group-containing (meth)acrylic polymerizable monomer (b); and a water-soluble polymerizable monomer (c), wherein the asymmetric acrylamide-methacrylic acid ester compound (a) is represented by the following general formula (1):

where X is an optionally substituted, linear or branched $C_1$ to $C_6$ aliphatic group or an optionally substituted aromatic group, the aliphatic group is optionally interrupted by at least one linking group selected from the group consisting of —O—, —S—, —CO—, —CO—O—, —O—CO—, —$NR^1$—, —CO—$NR^1$—, —$NR^1$—CO—, —CO—O—$NR^1$—, —O—CO—$NR^1$—, and —$NR^1$—CO—$NR^1$—, and $R^1$ is a hydrogen atom or an optionally substituted, linear or branched $C_1$ to $C_6$ aliphatic group.

Preferably, the dental adhesive contains the asymmetric acrylamide-methacrylic acid ester compound (a) represented by the above formula (1) in which X is an optionally substituted, linear or branched $C_1$ to $C_4$ aliphatic group. Preferably, the dental adhesive contains the asymmetric acrylamide-methacrylic acid ester compound (a) represented by the above formula (1) in which X is an optionally substituted, linear or branched $C_2$ to $C_4$ aliphatic group, and $R^1$ is a hydrogen atom. The dental adhesive may further contain a hydrophobic crosslinkable polymerizable monomer (d). In the dental adhesive, the acid group-containing (meth)acrylic polymerizable monomer (b) is preferably a phosphate group-containing (meth)acrylic polymerizable monomer. In the dental adhesive, the water-soluble polymerizable monomer (c) preferably contains at least one selected from the group consisting of a monofunctional (meth)acrylamide compound (c-1), 2-hydroxyethyl (meth)acrylate, 2,3-dihydroxypropyl (meth)acrylate, and diacetone (meth)acrylamide, the monofunctional (meth)acrylamide compound (c-1) being represented by the following general formula (2):

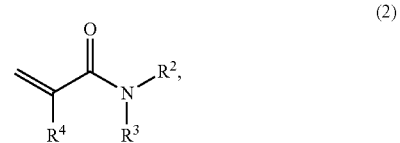

(2)

where $R^2$ and $R^3$ are each independently an optionally substituted, linear or branched $C_1$ to $C_3$ alkyl group, and $R^4$ is a hydrogen atom or a methyl group. Furthermore, in the dental adhesive, the weight ratio between the water-soluble polymerizable monomer (c) and the asymmetric acrylamide-methacrylic acid ester compound (a) is preferably 10:1 to 1:10.

Advantageous Effects of Invention

The dental adhesive of the present invention exhibits excellent initial bond strength and bond durability to both dentin and enamel. The dental adhesive of the present invention has good storage stability due to high compatibility of the components and thus low likelihood of separation thereof.

DESCRIPTION OF EMBODIMENTS

The dental adhesive of the present invention contains, as essential components, an asymmetric acrylamide-methacrylic acid ester compound (a) represented by the above general formula (1), an acid group-containing (meth)acrylic polymerizable monomer (b), and a water-soluble polymerizable monomer (c). As used in the present description, "(meth)acrylate" collectively refers to acrylate and methacrylate. The same applies to similar expressions.

The present invention is characterized in that an asymmetric acrylamide-methacrylic acid ester compound (a) represented by the above general formula (1) having two polymerizable groups, one of which is a methacrylic acid ester group and the other of which is an acrylamide group as a secondary amide group is used (hereinafter, in the present description, a compound having two polymerizable groups bonded to a group represented by X, one of which is a methacrylic acid ester group and the other of which is an acrylamide group as a secondary amide group, is referred to as an "asymmetric acrylamide-methacrylic acid ester compound" for the sake of convenience).

It is not known exactly why a dental adhesive of the present invention containing an asymmetric acrylamide-methacrylic acid ester compound (a) exhibits high initial bond strength and bond durability. The reasons for this are probably as follows. The asymmetric acrylamide-methacrylic acid ester compound (a) of the present invention has high hydrophilicity derived from amide protons and thus easily penetrates into the collagen layer of dentin. In addition, two polymerizable groups in the molecule of this compound (a), that is, an acrylamide group and a methacrylic acid ester group have relatively similar and balanced curing rates and thus the compound (a) exhibits sufficient curability and the penetrating bonding material forms a solid layer. In general, when an acrylic acid ester and a methacrylic acid ester have the same skeleton, the acrylic acid ester that has no methyl group and thus is sterically unhindered is more reactive than the methacrylic acid ester. The same applies to an acrylamide and a methacrylamide. Furthermore, the present inventors' studies have revealed that when a methacrylamide and a methacrylic acid ester have the same skeleton, the curing rate of the methacrylic acid ester tends to be higher than that of the methacrylamide. Therefore, when two polymerizable groups in the molecule are a methacrylic acid ester and a methacrylamide, the curing rate of the ester side tends to be higher than that of the amide side and thus their curing rates tend to be less balanced. Probably, in the asymmetric acrylamide-methacrylic acid ester compound (a) of the present invention, the curing rates between the ester side and the amide side is well balanced because an ester which is believed to have a higher curing rate is combined with a less reactive methacrylic group and an amide which is believed to have a lower curing rate is combined with a more reactive acrylic group. That is, the asymmetric acrylamide-methacrylic acid ester compound (a) can be considered as a compound having both high hydrophilicity derived from amide protons and high polymerization curability derived from two polymerizable groups having well-balanced curing rates.

For the reasons described above, a dental adhesive containing the asymmetric acrylamide-methacrylic acid ester compound (a) has not only high initial bond strength to dentin and enamel but also high bond durability thereto. In addition, the asymmetric acrylamide-methacrylic acid ester compound (a) of the present invention contains both an acrylamide group and a methacrylic acid ester group in the molecule, and thus has better compatibility with other polymerizable monomers. As a result, the resulting composition has higher homogeneity, and the problem of a decrease in the storage stability caused by the separation of the components during storage can be solved.

The asymmetric acrylamide-methacrylic acid ester compound (a) used in the present invention is described. This asymmetric acrylamide-methacrylic acid ester compound is represented by the following general formula (1) (hereinafter, an asymmetric acrylamide-methacrylic acid ester compound represented by the following general formula (1) is referred to as an "asymmetric acrylamide-methacrylic acid ester compound (a)"):

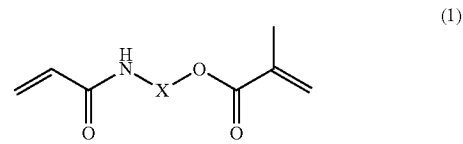

(1)

In this formula (1), X is an optionally substituted, linear or branched $C_1$ to $C_6$ aliphatic group or an optionally substituted aromatic group, and at least one linking group selected from the group consisting of —O—, —S—, —CO—, —CO—O—, —O—CO—, —NR$^1$—, —CO—NR$^1$—, —NR$^1$—CO—, —CO—O—NR$^1$—, —O—CO—NR$^1$—, and —NR$^1$—CO—NR$^1$— may be introduced into this aliphatic group. That is, the aliphatic group is optionally interrupted by at least one of the above-mentioned linking groups. $R^1$ is a hydrogen atom or an optionally substituted, linear or branched $C_1$ to $C_6$ aliphatic group.

X is a moiety for adjusting the hydrophilicity of the asymmetric acrylamide-methacrylic acid ester compound (a). The optionally substituted $C_1$ to $C_6$ aliphatic group represented by X may be a saturated aliphatic group (such as an alkylene group or a cycloalkylene group (for example, 1,4-cyclohexylene group)) or an unsaturated aliphatic group (such as an alkenylene group or an alkynylene group). In view of availability, ease of production, and chemical stability, it is preferable that the aliphatic group be a saturated aliphatic group (alkylene group). In view of adhesiveness to tooth structures and polymerization curability, X is preferably an optionally substituted, linear or branched $C_1$ to $C_4$ aliphatic group, and more preferably an optionally substituted, linear or branched $C_2$ to $C_4$ aliphatic group.

Examples of the $C_1$ to $C_6$ alkylene group include methylene, methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, tetramethylene, 1-butylethylene, 2-butylethylene, 1-ethyl-1-methylethylene, 1-ethyl-2-methylethylene, 1,1,2-trimethylethylene, 1,2,2-trimethylethylene, 1-ethyltrimethylene, 2-ethyltrimethylene, 3-ethyltrimethylene, 1,1-dimethyltrimethylene, 1,2-dimethyltrimethylene, 1,3-dimethyltrimethylene, 2,3-dimethyltrimethylene, 3,3-dimethyltrimethylene, 1-methyltetramethylene, 2-methyltetramethylene, 3-methyltetramethylene, 4-methyltetramethylene, pentamethylene, 1-butylethylene, 2-butylethylene, 1-methyl-1-propylethylene, 1-methyl-2-propylethylene, 2-methyl-2-propylethylene, 1,1-diethylethylene, 1,2-diethylethylene, 2,2-diethylethylene, 1-ethyl-1,2-dimethylethylene, 1-ethyl-2,2-dimethylethylene, 2-ethyl-1,1-dimethylethylene, 2-ethyl-1,2-dimethylethylene, 1,1,2,2-tetramethylethylene, 1-propyltrimethylene, 2-propyltrimethylene, 3-propyltrimethylene, 1-ethyl-1-methyltrimethylene, 1-ethyl-2-methyltrimethylene, 1-ethyl-3-methyltrimethylene, 2-ethyl-1-methyltrimethylene, 2-ethyl-2-methyltrimethylene, 2-ethyl-3-methyltrimethylene, 3-ethyl-1-methyltrimethylene, 3-ethyl-2-methyltrimethylene, 3-ethyl-3-methyltrimethylene, 1,1,2-trimethyltrimethylene, 1,1,3-trimethyltrimethylene, 1,2,2-trimethyltrimethylene, 1,2,3-trimethyltrimethylene, 1,3,3-trimethyltrimethylene, 2,2,3-trimethyltrimethylene, 2,3,3-trimethyltrimethylene, 1-ethyltetramethylene, 2-ethyltetramethylene, 3-ethyltetramethylene, 4-ethyltetramethylene, 1,1-dimethyltetramethylene, 1,2-dimethyltetramethylene, 1,3-dimethyltetramethylene, 1,4-dimethyltetramethylene, 2,2-dimethyltetramethylene, 2,3-dimethyltetramethylene, 2,4-dimethyltetramethylene, 3,3-dimethyltetramethylene, 3,4-dimethyltetramethylene, 4,4-thmethyltetramethylene, 1-methylpentamethylene, 2-methylpentamethylene, 3-methylpentamethylene, 4-methylpentamethylene, 5-methylpentamethylene, and hexamethylene groups. The $C_1$ to $C_6$ alkylene group is preferably a methylene, methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, or tetramethylene group, and more preferably a methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, or tetramethylene group.

Examples of the optionally substituted aromatic group represented by X include an aryl group and an aromatic heterocyclic group. An aryl group is more preferred than an aromatic heterocyclic group as the aromatic group mentioned above. The hetero ring of the aromatic heterocyclic group is usually unsaturated. The aromatic hetero ring is preferably a five-membered or six-membered ring. For example, a phenyl group is preferred as the aryl group. Examples of the aromatic heterocyclic group include furan, thiophene, pyrrole, oxazole, isoxazole, thiazole, isothiazole, imidazole, pyrazole, furazan, triazole, pyran, pyridine, pyridazine, pyrimidine, pyrazine, and 1,3,5-triazine groups. Among the aromatic groups mentioned above, a phenyl group is particularly preferred.

The aliphatic group as $R^1$ may be either a saturated aliphatic group (alkyl group) or an unsaturated aliphatic group (alkenyl or alkynyl group). In view of availability, ease of production, and chemical stability, the aliphatic group is preferably a saturated aliphatic group (alkyl group). Examples of the linear or branched $C_1$ to $C_6$ alkyl group as $R^1$ include methyl, ethyl, n-propyl, isopropyl, n-butyl, isobutyl, sec-butyl, tert-butyl, n-pentyl, isopentyl, sec-pentyl, neopentyl, tert-pentyl, 1-ethylpropyl, hexyl, isohexyl, 1,1-dimethylbutyl, 2,2-dimethylbutyl, 3,3-dimethylbutyl, and 2-ethylbutyl groups. The alkyl group is preferably, a methyl, ethyl, n-propyl, isopropyl, n-butyl, isobutyl, sec-butyl, tert-butyl, or the like.

$R^1$ is more preferably a hydrogen atom or an optionally substituted, linear or branched $C_1$ to $C_4$ alkyl group, and even more preferably a hydrogen atom or an optionally substituted, linear or branched $C_1$ to $C_3$ alkyl group.

When the aliphatic group as X is interrupted by the above-mentioned linking group(s), the number of the linking groups is not particularly limited. The number of the linking groups may be about 1 to 10, preferably 1, 2, or 3, and more preferably 1 or 2. In the above formula (1), it is preferable that the aliphatic group as X be not interrupted by two or more contiguous linking groups. That is, it is preferable that the linking groups be not adjacent to each other. The linking group is more preferably at least one linking group selected from the group consisting of —O—, —S—, —CO—, —CO—O—, —O—CO—, —NH—, —CO—NH—, —NH—CO—, —CO—O—NH—, —O—CO—NH—, and —NH—CO—NH—, and particularly preferably at least one linking group selected from the group consisting of —O—, —S—, —CO—, —NH—, —CO—NH—, and —NH—CO—.

The substituent in the above formula (1) is not particularly limited. For example, the substituent is preferably a halogen atom (fluorine, chlorine, bromine, or iodine atom), a carboxy group, a hydroxy group, an amino group, an amino group mono- or di-substituted by $C_1$ to $C_6$ alkyl group(s), an acyl group, an acyloxy group, an amide group, a $C_1$ to $C_3$ alkoxycarbonyl group, a $C_1$ to $C_6$ alkoxy group, a $C_1$ to $C_6$ alkylthio group, a $C_1$ to $C_6$ alkyl group, or the like, and more preferably a halogen atom (fluorine, chlorine, bromine, or iodine atom), a $C_1$ to $C_6$ alkyl group, or the like. The $C_1$ to $C_6$ alkoxycarbonyl group, the $C_1$ to $C_3$ alkoxy group, the $C_1$ to $C_6$ alkylthio group, and the $C_1$ to $C_6$ alkyl group mentioned above may be substituted by 1, 2, or 3 halogen atoms. Specific examples of the above-mentioned alkyl group are the same as those of $R^1$, and a linear or branched $C_1$ to $C_4$ alkyl group is preferred. The number of the substituents is not particularly limited. The number of the substituents may be about 1 to 8, and preferably 1, 2, or 3.

The specific examples of the asymmetric acrylamide-methacrylic acid ester compound (a) are not particularly limited, and include the following.

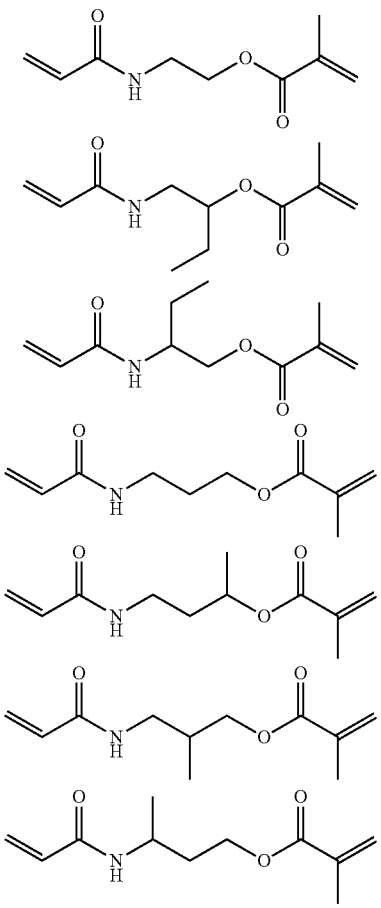

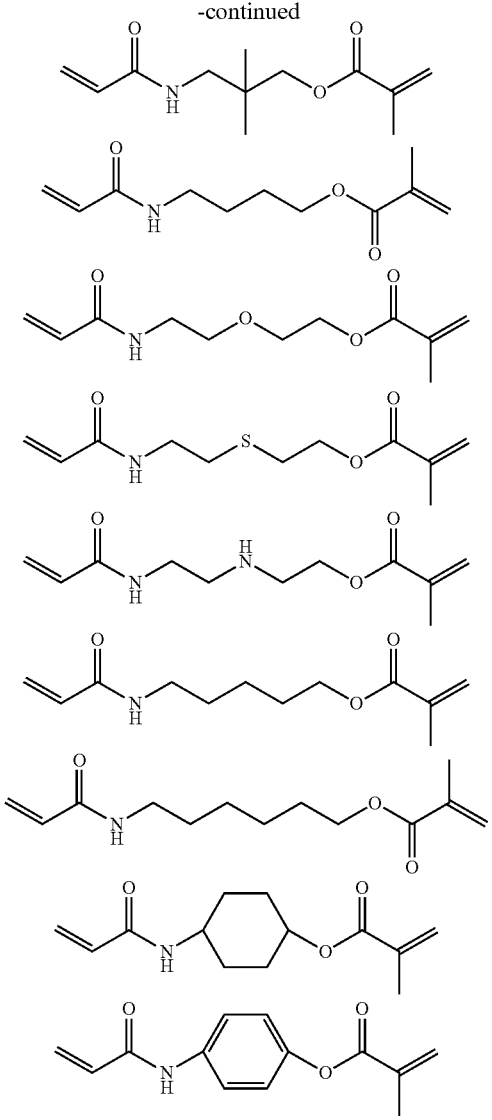

Among these, an asymmetric acrylamide-methacrylic acid ester compound having a linear or branched $C_2$ to $C_4$ aliphatic group as X is preferred in view of adhesiveness to tooth structures and polymerization curability. N-methacryloyloxyethyl acrylamide, N-methacryloyloxypropyl acrylamide, N-methacryloyloxybutyl acrylamide, N-(1-ethyl-(2-methacryloyloxy)ethyl) acrylamide, or N-(2-(2-methacryloyloxyethoxy)ethyl) acrylamide is more preferred. N-methacryloyloxyethyl acrylamide or N-methacryloyloxypropyl acrylamide is most preferred because of its high hydrophilicity responsible for penetration into the collagen layer of dentin.

One of the above-mentioned compounds may be contained alone as the asymmetric acrylamide-methacrylic acid ester compound (a), or a combination of two or more thereof may be contained as the asymmetric acrylamide-methacrylic acid ester compound (a). The content of the asymmetric acrylamide-methacrylic acid ester compound (a) is not particularly limited as long as the effect of the present invention can be obtained. The content of the asymmetric acrylamide-methacrylic acid ester compound (a) is preferably in the range of 1 to 60 weight %, more preferably in the range of 2 to 45 weight %, even more preferably in the range of 3 to 30 weight %, and particularly preferably in the range of 5 to 25 weight % with respect to the total weight of the dental adhesive (hereinafter, the "total weight of the dental adhesive" refers to the total weight of the dental adhesive including a polymerization initiator, a solvent, a polymerization accelerator, a polymerization inhibitor, a filler, and others).

Next, the acid group-containing (meth)acrylic polymerizable monomer (b) used in the present invention is described. In the present invention, the (meth)acrylic polymerizable monomer refers to a (meth)acrylate compound and/or a (meth)acrylamide compound.

The acid group-containing (meth)acrylic polymerizable monomer (b) demineralizes and penetrates into a tooth structure, and thus binds to the tooth structure. The acid-group-containing (meth)acrylic polymerizable monomer (b) is a polymerizable monomer having at least one of acid groups such as a phosphoric acid group, a phosphonic acid group, a pyrophosphoric acid group, a carboxylic acid group, and a sulfonic acid group and having at least one of an acryloyl group, a methacryloyl group, an acrylamide group, and a methacrylamide group. In view of adhesiveness to enamel, the acid group-containing (meth)acrylic polymerizable monomer (b) is preferably a monofunctional monomer having at least one of the above-mentioned acid groups and having any one of an acryloyl group, a methacryloyl group, an acrylamide group, and a methacrylamide group, as a polymerizable group. Specific examples thereof are as follows.

Examples of the phosphoric acid group-containing (meth)acrylic polymerizable monomer include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl] hydrogen phosphate, bis[4-(meth)acryloyloxybutyl] hydrogen phosphate, bis[6-(meth)acryloyloxyhexyl] hydrogen phosphate, bis[8-(meth)acryloyloxyoctyl] hydrogen phosphate, bis[9-(meth)acryloyloxynonyl] hydrogen phosphate, bis[10-(meth)acryloyloxydecyl] hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, 2-(meth)acryloyloxyethyl-(4-methoxyphenyl) hydrogen phosphate, and 2-(meth)acryloyloxypropyl-(4-methoxyphenyl) hydrogen phosphate; and their acid chlorides, alkali metal salts, ammonium salts, and amine salts.

Examples of the phosphonic acid group-containing (meth)acrylic polymerizable monomer include: 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, and 10-(meth)acryloyloxydecylphosphonoacetate; and their acid chlorides, alkali metal salts, ammonium salts, and amine salts.

Examples of the pyrophosphoric acid group-containing (meth)acrylic polymerizable monomer include: bis[2-(meth)

acryloyloxyethyl] pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate, and bis[10-(meth)acryloyloxydecyl] pyrophosphate; and their acid chlorides, alkali metal salts, ammonium salts, and amine salts.

Examples of the carboxylic acid group-containing (meth)acrylic polymerizable monomer include: (meth)acrylic acid, 4-(meth)acryloyloxyethoxycarbonylphthalic acid, 4-(meth)acryloyloxyethyl trimellitic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, and their acid anhydrides; and 5-(meth)acryloylaminopentylcarboxylic acid, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, 11-(meth)acryloyloxy-1,1-undecanedicarboxylic acid, and their acid chlorides, alkali metal salts, ammonium salts, and amine salts.

Examples of the sulfonic acid group-containing (meth)acrylic polymerizable monomer include 2-(meth)acrylamide-2-methylpropanesulfonic acid, 2-sulfoethyl (meth)acrylate, and their acid chlorides, alkali metal salts, ammonium salts and amine salts.

Among these acid group-containing (meth)acrylic polymerizable monomers (b), the phosphoric or pyrophosphoric acid group-containing (meth)acrylic polymerizable monomers are preferred since such monomers provide better bond strength to tooth structures. Particularly preferred are the phosphoric acid group-containing (meth)acrylic polymerizable monomers. Among the phosphoric acid group-containing (meth)acrylic polymerizable monomers, a divalent phosphoric acid group-containing (meth)acrylic polymerizable monomer that has as the main chain of the molecule an alkyl or alkylene group having 6 to 20 carbon atoms is more preferable, and a divalent phosphoric acid group-containing (meth)acrylic polymerizable monomer that has as the main chain of the molecule an alkylene group having 8 to 12 carbon atoms, such as 10-methacryloyloxydecyl dihydrogen phosphate, is most preferable.

One of the above-mentioned monomers may be contained alone as the acid group-containing (meth)acrylic polymerizable monomer (b), or a combination of two or more thereof may be contained as the acid group-containing (meth)acrylic polymerizable monomer (b). The content of the acid group-containing (meth)acrylic polymerizable monomer (b) is not particularly limited as long as the effect of the present invention can be obtained. However, in order to obtain higher bond strength, the content of the acid group-containing (meth)acrylic polymerizable monomer (b) is preferably in the range of 1 to 50 weight %, more preferably in the range of 1 to 30 weight %, and most preferably in the range of 3 to 20 weight %, with respect to the total weight of the dental adhesive.

Next, the water-soluble polymerizable monomer (c) used in the present invention is described.

In the context of the present invention, the water-soluble polymerizable monomer (c) refers to a polymerizable monomer, other than the asymmetric acrylamide-methacrylic acid ester compound (a) and the acid group-containing (meth)acrylic polymerizable monomer (b), having a solubility of 5 weight % or more in water at 25° C. The water-soluble polymerizable monomer (c) preferably has a solubility of 10 weight % or more, and more preferably a solubility of 15 weight % or more in water at 25° C. The water-soluble polymerizable monomer (c) promotes the penetration of the asymmetric acrylamide-methacrylic acid ester compound (a), the hydrophobic crosslinkable polymerizable monomer (d), and the polymerization initiator into a tooth structure. The monomer (c) itself also penetrates into a tooth structure and binds and adheres to an organic component (collagen) in the tooth structure.

Since the water-soluble polymerizable monomer (c) has water solubility, it has a hydrophilic group such as a hydroxyl group, an oxymethylene group, an oxyethylene group, an oxypropylene group, or an amide group. Examples of the water-soluble polymerizable monomer (c) include: water-soluble (meth)acrylate compounds such as 2-hydroxyethyl (meth)acrylate, 3-hydroxypropyl (meth)acrylate, 2-hydroxypropyl (meth)acrylate, 1,3-dihydroxypropyl (meth)acrylate, 2,3-dihydroxypropyl (meth)acrylate, 2-trimethylammoniumethyl (meth)acrylchloride, and polyethylene glycol di(meth)acrylate (having 9 or more oxyethylene groups); N-methylol (meth)acrylamide; N-hydroxyethyl (meth)acrylamide; N,N-(dihydroxyethyl) (meth)acrylamide; N-methoxymethyl (meth)acrylamide; N-ethoxymethyl (meth)acrylamide; diacetone (meth)acrylamide; 4-(meth)acryloylmorpholine; N-trihydroxymethyl-N-methyl (meth)acrylamide; and a monofunctional (meth)acrylamide compound (c-1) represented by the following general formula (2).

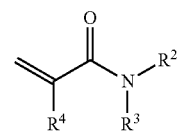

(2)

In the formula (2), $R^2$ and $R^3$ are each independently an optionally substituted, linear or branched $C_1$ to $C_3$ alkyl group, and $R^4$ is a hydrogen atom or a methyl group.

The same substituent in the formula (1) can be used as $R^2$ or $R^3$. Examples of the above-mentioned $C_1$ to $C_3$ alkyl group as $R^2$ or $R^3$ include a methyl group, an ethyl group, an n-propyl group, and an isopropyl group.

Among these water-soluble polymerizable monomers (c), in view of adhesiveness to tooth structures, 2-hydroxyethyl (meth)acrylate, 2,3-dihydroxypropyl (meth)acrylate, diacetone (meth)acrylamide, and a monofunctional (meth)acrylamide compound (c-1) are preferable, and a monofunctional (meth)acrylamide compound (c-1) is more preferable. One of the above-mentioned monomers may be contained alone as the water-soluble polymerizable monomer (c), or a combination of two or more thereof may be contained as the water-soluble polymerizable monomer (c).

Among the monofunctional (meth)acrylamide compounds (c-1), in view of storage stability, N,N-dimethylacrylamide and N,N-diethylacrylamide are more preferable, and N,N-diethylacrylamide is most preferable.

In the present invention, the content of the water-soluble polymerizable monomer (c) is not particularly limited as long as the effect of the present invention can be obtained. However, in order to obtain higher bond strength, the content of the water-soluble polymerizable monomer (c) is preferably in the range of 5 to 60 weight %, more preferably in the range of 7 to 50 weight %, even more preferably in the range of 10 to 45 weight %, and most preferably in the range of 13 to 40 weight %, with respect to the total weight of the dental adhesive.

In the present invention, the weight ratio ((c):(a)) between the water-soluble polymerizable monomer (c) and the asymmetric acrylamide-methacrylic acid ester compound (a) is preferably 10:1 to 1:10, more preferably 7:1 to 1:7, even more preferably 5:1 to 1:5, and particularly preferably 3:1 to 1:3. When the content of the water-soluble polymerizable monomer (c) is too high and causes the weight ratio to be higher than 10:1, the adhesiveness to dentin may be reduced. On the other hand, when the content of the asymmetric acrylamide-methacrylic acid ester compound (a) is too high and causes the weight ratio to be lower than 1:10, the bond strength to enamel may be reduced. In the case where the water-soluble polymerizable monomer (c) contains the monofunctional (meth)acrylamide compound (c-1) represented by the above formula (2), the weight ratio ((c-1):(a)) is preferably 10:1 to 1:10, more preferably 7:1 to 1:7, and even more preferably 4:1 to 1:4.

The hydrophobic crosslinkable polymerizable monomer (d) is a hydrophobic compound having no acid group and having at least two polymerizable groups per molecule. As used herein, the term "hydrophobicity" refers to a solubility of less than 5 weight % in water at 25° C. Examples of the hydrophobic crosslinkable polymerizable monomer (d) include aromatic compound-based bifunctional polymerizable monomers, aliphatic compound-based bifunctional polymerizable monomers, and tri- or higher-functional polymerizable monomers.

Examples of the aromatic compound-based bifunctional polymerizable monomer include 2,2-bis((meth)acryloyloxyphenyl)propane, 2,2-bis[4-(3-(meth)acryloyloxy-2-hydroxypropoxy)phenyl]propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, and 2,2-bis(4-(meth)acryloyloxyisopropoxyphenyl)propane. Among these, 2,2-bis[4-(3-(methacryloyloxy-2-hydroxypropoxy)phenyl]propane (commonly known as "Bis-GMA") is preferable.

Examples of the aliphatic compound-based bifunctional polymerizable monomer include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, and 2,2,4-trimethylhexamethylene bis(2-carbamoyloxyethyl) di(meth)acrylate. Among these, 2,2,4-trimethylhexamethylene bis(2-carbamoyloxyethyl) dimethacrylate (commonly known as "UDMA") is preferable.

Examples of the tri- or higher-functional polymerizable monomer include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)-bis[2-(aminocarboxy)propane-1,3-diol]tetra(meth)acrylate, and 1,7-diacryloyloxy-2,2,6,6-tetra(meth)acryloyloxymethyl-4-oxyheptane. Among these, N,N-(2,2,4-trimethylhexamethylene)-bis[2-(aminocarboxy)propane-1,3-diol]tetramethacrylate is preferable.

Among the above-mentioned hydrophobic crosslinkable polymerizable monomers (d), Bis-GMA and UDMA are more preferable, and Bis-GMA is even more preferable.

One of the above-mentioned monomers may be contained alone as the hydrophobic crosslinkable polymerizable monomer (d), or a combination of two or more thereof may be contained as the hydrophobic crosslinkable polymerizable monomer (d). The content of the hydrophobic crosslinkable polymerizable monomer (d) is not particularly limited as long as the effect of the present invention can be obtained. However, in order to provide not only high penetrability into a tooth structure and thus excellent bond strength but also sufficient strength to the composition, the content of the hydrophobic crosslinkable polymerizable monomer (d) is preferably in the range of 5 to 60 weight %, more preferably in the range of 10 to 50 weight %, even more preferably in the range of 12 to 40 weight %, and particularly preferably in the range of 15 to 30 weight %, with respect to the total weight of the dental adhesive.

The dental adhesive of the present invention may contain a polymerizable monomer other than the above-mentioned polymerizable monomers as long as the effect of the present invention is not impaired. The dental adhesive of the present invention may contain, as a polymerizable monomer, a symmetric (meth)acrylamide compound, an asymmetric bifunctional (meth)acrylamide compound, or the like. However, it is preferable that the dental adhesive contain no such compound (be substantially free of such a compound). In the present description, the phrase "being substantially free of a component" means that the dental adhesive of the present invention contains no such component or contains only traces of the component to the extent that the effect of the dental adhesive of the present invention is not impaired. The symmetric (meth)acrylamide compound is, for example, a compound represented by the above formula (3) or (4) (in these formulae, what the symbols stand for is as described above). Specific examples of the symmetric (meth)acrylamide compound include bis acrylamide ethylene and N,N-diethyl-1,3-propylene-bisacrylamide. The asymmetric bifunctional (meth)acrylamide compound is, for example, a compound represented by the above formula (5) (in this formula, what the symbols stand for is as described above). Specific examples of the asymmetric bifunctional (meth)acrylamide compound include N-ethyl-1,2-bis(acrylamide)ethane.

Depending on the specific embodiment employed, the dental adhesive of the present invention preferably contains a solvent. Examples of the solvent include water, an organic solvent, and a mixed solvent thereof.

The dental adhesive of the present invention containing water will promote the demineralizing action of the acid group-containing (meth)acrylic polymerizable monomer (b) on a tooth structure. The water used needs to be substantially free of impurities that adversely affect the adhesive properties. The water is preferably distilled water or ion-exchanged water. Having too low a water content could lead to a failure to provide a sufficient promoting effect on the demineralizing action, while having too high a water content could cause reduced bond strength. Thus, the water content is preferably in the range of 1 to 50 weight %, more preferably in the range of 5 to 30 weight %, and most preferably in the range of 10 to 20 weight %, with respect to the total weight of the dental adhesive.

The dental adhesive of the present invention containing an organic solvent will yield a further improvement in terms of adhesive properties, coating properties, and penetration into tooth structures, and the organic solvent contained will prevent the components of the composition from becoming separated from one another. The organic solvent used typically has a boiling point of 150° C. or lower at ordinary pressure and has a solubility of 5 weight % or more in water at 25° C. The organic solvent more preferably has a solubility of 30 weight % or more in water at 25° C. and is most preferably freely soluble in water at 25° C. as desired.

Examples of the organic solvent include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Among these, a water-soluble organic solvent is preferable as the organic solvent in view of both the safety for living organisms and the ease of removal utilizing volatility. To be specific, ethanol, 2-propanol, 2-methyl-2-propanol, acetone, and tetrahydrofuran are preferable. Ethanol, 2-propanol, 2-methyl-2-propanol, and tetrahydrofuran are more preferable. The content of the organic solvent is not particularly limited. Some embodiments have no need to contain the organic solvent. In embodiments using the organic solvent, the content of the organic solvent is preferably in the range of 1 to 70 weight %, more preferably in the range of 5 to 50 weight %, and most preferably in the range of 10 to 30 weight %, with respect to the total weight of the dental adhesive.

In view of the curability, the dental adhesive of the present invention preferably contains a polymerization initiator. The polymerization initiator used in the present invention can be a commonly-known polymerization initiator. In particular, one polymerization initiator for photopolymerization or chemical polymerization is used alone or two or more polymerization initiators for photopolymerization or chemical polymerization are used in appropriate combination.

Examples of the photopolymerization initiator include (bis)acylphosphine oxides, water-soluble acylphosphine oxides, thioxanthones, quaternary ammonium salts of thioxanthones, ketals, α-diketones, coumarins, anthraquinones, benzoin alkyl ether compounds, and α-aminoketone compounds.

Among the (bis)acylphosphine oxides that may be used as the photopolymerization initiator, examples of the acylphosphine oxide include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoykliphenylphosphine oxide, and benzoyl di-(2,6-dimethylphenyl) phosphonate. Examples of the bisacylphosphine oxide include bis-(2,6-dichlorobenzoyl) phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoylphenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoy)phenylphosphine oxide, and (2,5,6-trimethylbenzoyl)-2,4,4-trimethylpentylphosphine oxide.

The water-soluble acylphosphine oxide used as the photopolymerization initiator preferably has an alkali metal ion, an alkaline earth metal ion, a pyridinium ion, or an ammonium ion in the acylphosphine oxide molecule. For example, the water-soluble acylphosphine oxide can be synthesized by a method disclosed in EP 0009348 B1 or JP 57-197289 A.

Specific examples of the water-soluble acylphosphine oxide include sodium monomethyl acetylphosphonate, sodium monomethyl (1-oxopropyl)phosphonate, sodium monomethyl benzoylphosphonate, sodium monomethyl (1-oxobutyl)phosphonate, sodium monomethyl (2-methyl-1-oxopropyl)phosphonate, sodium acetylphosphonate, sodium monomethyl acetylphosphonate, sodium acetylmethylphosphonate, methyl 4-(hydroxymethoxyphosphinyl)-4-oxobutanoate sodium salt, methyl-4-oxo-phosphonobutanoate monosodium salt, acetylphenylphosphinate sodium salt, sodium (1-oxopropyl)pentylphosphinate, methyl-4-(hydroxypentylphosphinyl)-4-oxobutanoate sodium salt, sodium acetylpentylphosphinate, sodium acetylethylphosphinate, sodium methyl(1,1-dimethyl)methylphosphinate, sodium (1,1-dimethoxyethyl)methylphosphinate, sodium (1,1-diethoxyethyl)methylphosphinate, methyl-4-(hydroxymethylphosphinyl)-4-oxobutanoate lithium salt, 4-(hydroxymethylphosphinyl)-4-oxobutanoic acid dilithium salt, methyl(2-methyl-1,3-dioxolan-2-yl)phosphinate sodium salt, methyl(2-methyl-1,3-thiazolidin-2-yl)phosphonate sodium salt, (2-methylperhydro-1,3-diazin-2-yl)phosphonite sodium salt, acetylphosphinate sodium salt, (1,1-diethoxyethyl)phosphonite sodium salt, (1,1-diethoxyethyl) methylphosphonite sodium salt, methyl(2-methyloxathiolan-2-yl)phosphinate sodium salt, methyl(2,4,5-trimethyl-1,3-dioxolan-2-yl)phosphinate sodium salt, methyl(1,1-propoxyethyl)phosphinate sodium salt, (1-methoxyvinyl)methylphosphinate sodium salt, (1-ethylthiovinyl)methylphosphinate sodium salt, methyl(2-methylperhydro-1,3-diazin-2-yl)phosphinate sodium salt, methyl (2-methylperhydro-1,3-thiazin-2-yl)phosphinate sodium salt, methyl(2-methyl-1,3-diazolidin-2-yl)phosphinate sodium salt, methyl(2-methyl-1,3-thiazolidin-2-yl)phosphinate sodium salt, (2,2-dicyano-1-methylethynyl)phosphinate sodium salt, acetylmethylphosphinate oxime sodium salt, acetylmethylphosphinate-O-benzyloxyme sodium salt, 1-[(N-ethoxyimino)ethyl]methylphosphinate sodium salt, methyl(1-phenyliminoethyl)phosphinate sodium salt, methyl(1-phenylhydrazonoethyl)phosphinate sodium salt, [1-(2,4-dinitrophenylhydrazono)ethyl]methylphosphinate sodium salt, acetylmethylphosphinate semicarbazone sodium salt, (1-cyano-1-hydroxyethyl)methylphosphinate sodium salt, (dimethoxymethyl)methylphosphinate sodium salt, formylmethylphosphinate sodium salt, (1,1-dimethoxypropyl)methylphosphinate sodium salt, methyl(1-oxopropyl)phosphinate sodium salt, (1,1-dimethoxypropyl)methylphosphinate dodecylguanidine salt, (1,1-dimethoxypropyl) methylphosphinate isopropylamine salt, acetylmethylphosphinate thiosemicarbazone sodium salt, 1,3,5-tributyl-4-methylamino-1,2,4-triazolium(1,1-dimethoxyethyl)-methylphosphinate, 1-butyl-4-butylaminomethylamino-3,5-dipropyl-1,2,4-triazolium (1,1-dimethoxyethyl)-methylphosphinate, 2,4,6-trimethylbenzoylphenylphosphine oxide sodium salt, 2,4,6-trimethylbenzoylphenylphosphine oxide potassium salt, and 2,4,6-trimethylbenzoylphenylphosphine oxide ammonium salt. Examples of the water-soluble acylphosphine oxide further include compounds as specified in JP 2000-159621 A.

Among these (bis)acylphosphine oxides and water-soluble acylphosphine oxides, 2,4,6-trimethylbenzoyklipheylphosphine oxide, 2,4,6-trimethylbenzoylmethoxyphenylphosphine oxide, bis-(2,4,6-trimethylbenzoyl)

phenylphosphine oxide, and 2,4,6-trimethylbenzoylphenylphosphine oxide sodium salt are particularly preferable.

Examples of the thioxanthones and the quaternary ammonium salts of thioxanthones that may be used as the photopolymerization initiator include thioxanthone, 2-chlorothioxanthen-9-one, 2-hydroxy-3-(9-oxo-9H-thioxanthen-4-yloxy)-N,N,N-trimethyl-propanaminium chloride, 2-hydroxy-3-(1-methyl-9-oxo-9H-thioxanthen-4-yloxy)-N,N,N-trimethyl-propanaminium chloride, 2-hydroxy-3-(9-oxo-9H-thioxanthen-2-yloxy)-N,N,N-trimethyl-propanaminium chloride, 2-hydroxy-3-(3,4-dimethyl-9-oxo-9H-thioxanthen-2-yloxy)-N,N,N-trimethyl-1-propanaminium chloride, 2-hydroxy-3-(3,4-dimethyl-9H-thioxanthen-2-yloxy)-N,N,N-trimethyl-1-propanaminium chloride, and 2-hydroxy-3-(1,3,4-trimethyl-9-oxo-9H-thioxanthen-2-yloxy)-N,N,N-trimethyl-1-propanaminium chloride.

A particularly preferred thioxanthone among the above-mentioned thioxanthones is 2-chlorothioxanthen-9-one, and a particularly preferred quaternary ammonium salt of a thioxanthone among the above-mentioned quaternary ammonium salts of thioxanthones is 2-hydroxy-3-(3,4-dimethyl-9H-thioxanthen-2-yloxy)-N,N,N-trimethyl-1-propanaminium chloride.

Examples of the ketals that may be used as the photopolymerization initiator include benzyl dimethyl ketal and benzyl diethyl ketal.

Examples of the α-diketones that may be used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Particularly preferred among these is camphorquinone, since it shows maximum absorption at a wavelength in the visible region.

Examples of the coumarin compounds that may be used as the photopolymerization initiator include compounds disclosed in JP 9-3109 A and JP 10-245525 A, such as 3,3'-carbonylbis(7-diethylamino)coumarin, 3-(4-methoxybenzoyl)coumarin, 3-thenoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl)coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphto[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H, 5H, 11H-[1]benzopyrano[6,7,8-ij]quinolizin-11-one, and 10-(2-benzothiazoyl)-2,3,6,7-tetrahydro-1,1,7,7-tetramethyl-1H, 5H, 11H-[1]benzopyrano[6,7,8-ij]quinolizin-11-one.

Among the above-mentioned coumarin compounds, 3,3'-carbonylbis(7-diethylaminocoumarin) and 3,3'-carbonylbis(7-dibutylaminocoumarin) are preferable.

Examples of the anthraquinones that may be used as the photopolymerization initiator include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ethers that may be used as the photopolymerization initiator include benzoin methyl ether, benzoin ethyl ether, benzoin isopropyl ether, and benzoin isobutyl ether.

Examples of the α-aminoketones that may be used as the photopolymerization initiator include 2-methyl-1-[4-(methylthio)phenyl]-2-morpholinopropan-1-one.

It is preferable to use, among these photopolymerization initiators, at least one selected from the group consisting of (bis)acylphosphine oxides, salts thereof, α-diketones, and coumarin compounds. The use of such a photopolymerization initiator makes it possible to obtain a dental adhesive that has excellent photocurability in the visible and near-ultraviolet regions and thus exhibits sufficiently high photocurability regardless of which light source among a halogen lamp, light-emitting diode (LED), and xenon lamp is used.

An organic peroxide is preferably used as the chemical polymerization initiator among the polymerization initiators used in the present invention. The organic peroxide used as the chemical polymerization initiator is not particularly limited, and can be a commonly-known organic peroxide. Typical examples of the organic peroxide include ketone peroxides, hydroperoxides, diacyl peroxides, dialkyl peroxides, peroxyketals, peroxyesters, and peroxyclicarbonates.

Examples of the ketone peroxides that may be used as the chemical polymerization initiator include methyl ethyl ketone peroxide, methyl isobutyl ketone peroxide, methylcyclohexanone peroxide, and cyclohexanone peroxide.

Examples of the hydroperoxides that may be used as the chemical polymerization initiator include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides that may be used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides that may be used as the chemical polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexine.

Examples of the peroxyketals that may be used as the chemical polymerization initiator include 1,1-bis(t-butylperoxy)-3,3,5-trimethylcyclohexane, 1,1-bis(t-butylperoxy)cyclohexane, 2,2-bisq-butylperoxykutane, 2,2-bis(t-butylperoxy)octane, and n-butyl 4,4-bis(t-butylperoxy)valerate.

Examples of the peroxyesters that may be used as the chemical polymerization initiator include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxymaleic acid.

Examples of the peroxydicarbonates that may be used as the chemical polymerization initiator include di-3-methoxy peroxydicarbonate, di-2-ethylhexyl peroxydicarbonate, bis (4-t-butylcyclohexyl) peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, the diacyl peroxides are preferably used in view of the overall balance of safety, storage stability, and radical formation potential. Among the diacyl peroxides, benzoyl peroxide is particularly preferably used.

One of the above-mentioned polymerization initiators may be used alone, or two or more thereof may be used in combination. The content of the polymerization initiator used in the present invention is not particularly limited. In view of the curability, etc. of the resulting composition, the content of the polymerization initiator is preferably in the range of 0.01 to 10 weight %, more preferably in the range of 0.05 to 7 weight %, and most preferably in the range of 0.1 to 5 weight %, with respect to the total weight of the dental adhesive. When the content of the polymerization initiator exceeds 10 weight %, if the polymerization initiator itself has low polymerization performance, sufficient bond strength may not be obtained and even deposition of the components of the composition may occur.

In a preferred embodiment, the polymerization initiator is used in combination with a polymerization accelerator. Examples of the polymerization accelerator that may be used in the present invention include amines, sulfinic acids, sulfinates, borate compounds, barbituric acid derivatives, triazine compounds, copper compounds, tin compounds, vanadium compounds, halogen compounds, aldehydes, thiol compounds, sulfites, hydrogen sulfites, and thiourea compounds.

Amines that may be used as the polymerization accelerator include aliphatic amines and aromatic amines. Examples of the aliphatic amine include: primary aliphatic amines such as n-butylamine, n-hexylamine, and n-octylamine; secondary aliphatic amines such as diisopropylamine, dibutylamine, and N-methylethanolamine; tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferably used in view of the curability and storage stability of the composition, and in particular, N-methyldiethanolamine and triethanolamine are more preferably used.

Examples of the aromatic amine include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[(meth)acryloyloxy]ethyl 4-(N,N-dimethylamino) benzoate, 4-(N,N-dimethylamino)benzophenone, and butyl 4-dimethylaminobenzoate. Among these, at least one selected from the group consisting of N,N-di(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone is preferably used in view of their ability to impart high curability to the composition.

Examples of the sulfinic acids and sulfinates that may be used as the polymerization accelerator include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Particularly preferred are sodium benzenesulfinate, sodium p-toluenesulfinate, and sodium 2,4,6-triisopropylbenzenesulfinate.

The borate compound used as the polymerization accelerator is preferably an aryl borate compound. Specific examples of aryl borate compounds that are suitable for use as the polymerization accelerator include borate compounds having one aryl group per molecule, such as trialkylphenylboron, trialkyl(p-chlorophenyl)boron, trialkyl(p-fluorophenyl)boron, trialkyl[(3,5-bistrifluoromethyl)phenyl]boron, trialkyl[3,5-bis(1,1,1,3,3,3-hexafluoro-2-methoxy-2-propyl) phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, and trialkyl(m-octyloxyphenyl)boron (their alkyl groups are each at least one selected from the group consisting of, for example, an n-butyl group, an n-octyl group, and an n-dodecyl group), and their sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts.

Examples of the borate compound include those that have two aryl groups per molecule, such as dialkyldiphenylboron, dialkyldi(p-chlorophenyl)boron, dialkyldi(p-fluorophenyl) boron, dialkyl[di(3,5-bis-trifluoromethyl)phenyl]boron, dialkyldi[3,5-bis(1,1,1,3,3,3-hexafluoro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron, and dialkyldi(m-octyloxyphenyl)boron (their alkyl groups are each at least one selected from the group consisting of, for example, an n-butyl group, an n-octyl group, and an n-dodecyl group), and their sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts.

Examples of the borate compound further include those that have three aryl groups per molecule, such as monoalkyltriphenylboron, monoalkyltri(p-chlorophenyl)boron, mono alkyltri(p-fluorophenyl)boron, monoalkyltri(3,5-bis-trifluoromethyl)phenylboron, monoalkyltri[3,5-bis(1,1,1,3,3,3-hexafluoro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, and monoalkyltri(m-octyloxyphenyl) boron (their alkyl groups are each at least one selected from, for example, an n-butyl group, an n-octyl group, and an n-dodecyl group), and their sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts.

Examples of the borate compound further include those that have four aryl groups per molecule, such as tetraphenylboron, tetrakis(p-chlorophenyl)boron, tetrakis(p-fluorophenyl)boron, tetrakis[(3,5-bistrifluoromethyl)phenyl]boron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, [(3,5-bistrifluoromethyl)phenyl]triphenylboron, (p-nitrophenyl)triphenylboron, (m-butyloxyphenyl)triphenylboron, (p-butyloxyphenyntriphenylboron, (m-octyloxyphenyl)triphenylboron, and (p-octyloxyphenyl)triphenylboron, and their sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts.

In view of storage stability, it is more preferable to use the borate compounds having three or four aryl groups per molecule among the above-mentioned aryl borate compounds. One of these aryl borate compounds may be used alone or a mixture of two or more thereof may be used.

Examples of the barbituric acid derivatives that may be used as the polymerization accelerator include: barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-5-n-butylbarbituric acid, 1,3-dimethyl-5-isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, and thiobarbituric acids; and salts of the barbituric acids (alkali metal salts and alkaline earth metal salts are particularly preferable). Examples of the salts of the barbituric acids include sodium 5-butylbarbiturate, sodium 1,3,5-trimethylbarbiturate, and sodium 1-cyclohexyl-5-ethylbarbiturate.

Examples of particularly preferred barbituric acid derivatives include 5-butylbarbituric acid, 1,3,5-trimethylbarbituric acid, 1-cyclohexyl-5-ethylbarbituric acid, 1-benzyl-5-phenylbarbituric acid, and sodium salts of these barbituric acids.

Examples of the triazine compounds that may be used as the polymerization accelerator include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Among the triazine compounds mentioned above as examples, 2,4,6-tris(trichloromethyl)-s-triazine is particularly preferable in terms of polymerization activity. In terms of storage stability, 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine are particularly preferable. The above triazine compounds may be used alone or a mixture of two or more thereof may be used.

Examples of the copper compounds that are suitable for use as the polymerization accelerator include copper acetylacetonate, copper (II) acetate, copper oleate, copper (II) chloride, and copper (II) bromide.

Examples of the tin compounds that may be used as the polymerization accelerator include di-n-butyltin dimaleate, di-n-octyltin dimaleate, di-n-octyltin dilaurate, and di-n-butyltin dilaurate. Particularly preferred tin compounds are di-n-octyltin dilaurate and di-n-butyltin dilaurate.

The vanadium compound used as the polymerization accelerator is preferably a compound of tetravalent and/or pentavalent vanadium. Examples of the compound of tetravalent and/or pentavalent vanadium include compounds mentioned in JP 2003-96122 A, such as divanadium (IV) tetroxide, vanadium (IV) oxide acetylacetonate, vanadyl (IV) oxalate, vanadyl (IV) sulfate, oxobis(1-phenyl-1,3-butanedionato)vanadium (IV), bis(maltolato)oxovanaclium (IV), vanadium (V) pentoxide, sodium metavanadate (V), and ammonium metavanadate (V).

Examples of the halogen compounds that are suitable for use as the polymerization accelerator include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes that may be used as the polymerization accelerator include terephthalaldehyde and benzaldehyde derivatives. Examples of the benzaldehyde derivatives include dimethylaminobenzaldehyde, p-methyloxybenzaldehyde, p-ethyloxybenzaldehyde, and p-n-octyloxybenzaldehyde. Among these, p-n-octyloxybenzaldehyde is preferably used in view of curability.

Examples of the thiol compounds that may be used as the polymerization accelerator include 3-mercaptopropyltrimethoxysilane, 2-mercaptobenzoxazole, decanethiol, and thiobenzoic acid.

Examples of the sulfites that may be used as the polymerization accelerator include sodium sulfite, potassium sulfite, calcium sulfite, and ammonium sulfite.

Examples of the hydrogen sulfites that may be used as the polymerization accelerator include sodium hydrogen sulfite and potassium hydrogen sulfite.

Examples of the thiourea compounds that may be used as the polymerization accelerator include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

One of the above-mentioned polymerization accelerators may be used alone, or two or more thereof may be used in combination. The content of the polymerization accelerator used in the present invention is not particularly limited. In view of the curability, etc. of the resulting composition, the content of the polymerization accelerator is preferably in the range of 0.01 to 10 weight %, more preferably in the range of 0.05 to 7 weight %, and most preferably in the range of 0.1 to 5 weight %, with respect to the total weight of the dental adhesive. When the content of the polymerization accelerator exceeds 10 weight %, if the polymerization initiator itself has low polymerization performance, sufficient bond strength may not be obtained.

Depending on the embodiment employed, the dental adhesive of the present invention preferably further contains a filler. Fillers are typically classified broadly into an organic filler, an inorganic filler, and an organic-inorganic composite filler.

Examples of the material of the organic filler include polymethyl methacrylate, polyethyl methacrylate, methyl methacrylate-ethyl methacrylate copolymer, cross-linked polymethyl methacrylate, cross-linked polyethyl methacrylate, polyamide, polyvinyl chloride, polystyrene, chloroprene rubber, nitrile rubber, ethylene-vinyl acetate copolymer, styrene-butadiene copolymer, acrylonitrile-styrene copolymer, and acrylonitrile-styrene-butadiene copolymer. These may be used alone or a mixture of two or more thereof may be used. The shape of the organic filler is not particularly limited, and the particle diameter of the filler used can be selected as appropriate. In view of the characteristics such as handling properties and mechanical strength of the resulting composition, the average particle diameter of the organic filler is preferably 0.001 to 50 µm and more preferably 0.001 to 10 µm. In the present description, the average particle diameter of the filler means the average particle diameter of the primary particles of the filler (i.e., the average primary particle diameter).

Examples of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone or a mixture of two or more thereof may be used. The shape of the inorganic filler is not particularly limited, and the particle diameter of the filler used can be selected as appropriate. In view of the characteristics such as handling properties and mechanical strength of the resulting composition, the average particle diameter of the inorganic filler is preferably 0.001 to 50 µm and more preferably 0.001 to 10 µm.

Examples of the shape of the inorganic filler include an irregular shape and a spherical shape. It is preferable to use a spherical filler as the inorganic filler in order to enhance the mechanical strength of the composition. The term "spherical filler" as used herein refers to a filler whose particles are rounded in shape as observed in a unit area of field of view in a photograph of the filler taken by a scanning electron microscope (which will hereinafter be abbreviated as "SEM") and have an average aspect ratio of 0.6 or more calculated as an average of values determined by dividing a diameter of each particle in a direction perpendicular to the maximum diameter of the particle by the maximum diameter. The average particle diameter of the spherical filler is preferably 0.1 µm or more in order to prevent a decrease in the degree of filling of the spherical filler in the composition and thus to maintain the mechanical strength. The average particle diameter of the spherical filler is also preferably 5 µm or less in order to obtain a sufficient surface area of the spherical filler and thus to maintain the mechanical strength of the resulting cured product.

The inorganic filler may be surface-treated beforehand with a commonly-known surface treatment agent such as a silane coupling agent where necessary in order to adjust the flowability of the composition. Examples of the surface treatment agent include vinyltrimethoxysilane, vinyltriethoxysilane, vinyltrichlorosilane, vinyltri(δ-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler used in the present invention is obtainable by adding a monomer compound to the above inorganic filler, forming the mixture into a paste, then subjecting the paste to polymerization, and grinding the resulting polymerization product. The organic-inorganic composite filler used can be, for example, a TMPT filler (obtainable by mixing trimethylolpropane methacrylate and a silica filler, subjecting the mixture to polymerization, and then grinding the resulting polymerization product). The shape of the organic-inorganic composite filler is not particularly limited, and the particle diameter of the filler used can be selected as appropriate. In view of the characteristics such as handling properties and mechanical strength of the resulting composition, the average particle diameter of the organic-inorganic composite filler is preferably 0.001 to 50 µm and more preferably 0.001 to 10 µm.

In the present description, the average particle diameter of the filler can be determined by the laser diffraction scattering method or by electron microscopic observation of the particles. Specifically, the laser diffraction scattering method is convenient for particle diameter measurement of particles with a diameter of 0.1 lam or more, and the electron microscopic observation is convenient for particle diameter measurement of ultrafine particles with a diameter of 0.1 µm or less. 0.1 lam is the value measured by the laser diffraction scattering method.

To be more specific about the laser diffraction scattering method, for example, the average particle diameter can be measured using a laser diffraction particle size distribution analyzer (SALD-2100, manufactured by Shimadzu Corporation) and using a 0.2% aqueous solution of sodium hexametaphosphate as a dispersion medium.

To be more specific about the electron microscopic observation, for example, the average particle diameter can be measured by taking a photograph of the particles with a scanning electron microscope (S-4000, manufactured by Hitachi, Ltd.) and measuring the particle diameters of (200 or more) particles observed in a unit area of field of view in the photograph by the use of an image-analyzing particle size distribution analysis software (MacView manufactured by Mountech Co., Ltd.). In this case, the particle diameter of each particle is obtained as an arithmetic mean value of the longest and shortest dimensions thereof, and the average primary particle diameter is calculated from the number of the particles and their particle diameters.

In the present invention, two or more fillers having different materials, particle size distributions, and forms may be mixed or combined for use. Particles other than the filler particles may be unintentionally contained as impurities, as long as the effect of the present invention is not impaired. In the present invention, a commercially available product may be used as the filler.

The content of the filler used in the present invention is not particularly limited. The content of the filler is preferably in the range of 0.1 to 30 weight %, more preferably in the range of 0.5 to 20 weight %, and most preferably in the range of 1 to 10 weight %, with respect to the total weight of the dental adhesive.

The dental adhesive may contain a fluorine ion-releasing material to impart acid resistance to a tooth structure. Examples of the fluorine ion-releasing material include: fluorine glass materials such as fluoroaluminosilicate glass; metal fluorides such as sodium fluoride, potassium fluoride, sodium monofluorophosphate, lithium fluoride, and ytterbium fluoride; fluorine ion-releasing polymers such as a copolymer of methyl methacrylate and fluoride methacrylate; and cetylamine hydrofluoride. One of these fluorine ion-releasing materials may be contained alone, or two or more of them may be contained in combination.

Furthermore, the dental adhesive of the present invention may contain, for example, a pH adjuster, a polymerization inhibitor, an ultraviolet absorber, a thickener, a colorant, a fluorescent agent, or a flavor as long as the effect of the present invention is not impaired. Additionally, the dental adhesive may contain an antibacterial substance such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, or triclosan.

The dental adhesive of the present invention exhibits excellent initial bond strength and bond durability to both enamel and dentin. The dental adhesive of the present invention has good storage stability due to high compatibility of the components and thus low likelihood of separation thereof. Furthermore, in the dental adhesive of the present invention, the cured bonding material has a low water absorption of 5.0% or less. Thus, a time-dependent decrease in the strength of the cured bonding material due to absorption of water is less likely to occur and the excellent bond durability can be maintained for a long period of time. The water absorption is preferably 4.5% or less, and more preferably 4.0% or less. The method for measuring the percentage of water absorption is as described in Examples to be described below.

The dental adhesive of the present invention can be used for dental adhesives such as a primer and a bonding material. In this case, the composition may be used as a two-part product including two bottles of different components of the composition.

The asymmetric acrylamide-methacrylic acid ester compound (a) used in the present invention contains amide protons, and thus has high hydrophilicity and easily penetrates into the collagen layer of dentin. Therefore, the dental adhesive of the present invention containing the asymmetric acrylamide-methacrylic acid ester compound (a) can be used particularly suitably as a dental primer. Furthermore, the dental adhesive of the present invention containing the acid group-containing (meth)acrylic polymerizable monomer (b) can be used as a dental self-etching primer.

Preferably, a primer using the dental adhesive of the present invention is a composition containing the asymmetric acrylamide-methacrylic acid ester compound (a), the acid group-containing (meth)acrylic polymerizable monomer (b), the water-soluble polymerizable monomer (c), and a solvent. Furthermore, the combined use of the polymerization initiator and the polymerization accelerator also is a preferred embodiment, and an amine is preferably used as the polymerization accelerator.

It is preferable that the solvent be used in the form of a mixed solvent of water and an organic solvent. The content of water in the mixed solvent is not particularly limited. The content of water is preferably 10 weight % or more, and more preferably 30 weight % or more. Depending on the embodiment employed, the primer need not contain any organic solvent.

The adhesive of the present invention can particularly suitably be used as a bonding material. A bonding material in a "two-step adhesive system" in which a primer and a bonding material are used in combination is preferably a composition containing the asymmetric acrylamide-methacrylic acid ester compound (a), the acid group-containing (meth)acrylic polymerizable monomer (b), the water-soluble polymerizable monomer (c), the hydrophobic crosslinkable polymerizable monomer (d), a polymerization initiator, and a filler. The use of a polymerization accelerator is also a preferred embodiment, and an amine is preferably used as the polymerization accelerator.

Since the dental adhesive of the present invention contains highly hydrophilic amide protons, it easily penetrates into the collagen layer of dentin. In addition, since the dental adhesive of the present invention contains the asymmetric acrylamide-methacrylic acid ester compound (a) having a plurality of polymerizable groups and thus having high curability and the acid group-containing (meth)acrylic polymerizable monomer (b), it can be advantageously applied to a "one-step adhesive system" in which three steps of "demineralization", "penetration", and "curing" are performed in one operation. Two typical products of bonding materials used in such a one-step adhesive system are: a bonding material including two different liquids, a liquid A and a liquid B, to be mixed together immediately before use; and a bonding material of the so-called "one-part one-step adhesive system" prepared in the form of one liquid. In particular, the use of the one-part product is more advantageous because the process is further simplified. Therefore, it is most preferable to use the dental adhesive of the present invention as a one-part bonding material. When the dental adhesive of the present invention is used as a one-part bonding material of a one-step adhesive system, it is preferable that the composition be a composition containing the asymmetric acrylamide-methacrylic acid ester compound (a), the acid group-containing (meth)acrylic polymerizable monomer (b), the water-soluble polymerizable monomer (c), the hydrophobic crosslinkable polymerizable monomer (d), a polymerization initiator, a filler, and a solvent, and it is more preferable that such a composition further contain a monofunctional (meth)acrylamide compound (c-1) as the water-soluble polymerizable monomer (c). In the one-part one-step adhesive system, since the "penetration" and "curing" are performed in one operation. Therefore, the use of a polymerizable monomer having high hydrophilicity derived from amide protons and having two polymerizable groups with balanced curing rates, like the asymmetric acrylamide-methacrylic acid ester compound (a), is of great significance.

Furthermore, the combined use of the polymerization initiator and the polymerization accelerator also is a preferred embodiment, and an amine is preferably used as the polymerization accelerator.

In the one-part one-step adhesive system, all the processes of demineralization, penetration, and curing need to be performed using one liquid in one step. Therefore, if priority is given to the penetrability, it is preferable that the dental adhesive contain water as the solvent. On the other hand, if priority is given to the curability, it is preferable that the dental adhesive contain an appropriate amount of the hydrophobic crosslinkable polymerizable monomer (d). In order to obtain a homogeneous solution, it is preferable that the dental adhesive contain an organic solvent as the solvent. The use of the solvent in the form of a mixed solvent of water and an organic solvent is a more preferred embodiment. In this embodiment, the content of water in the mixed solvent is preferably 5 weight % or more, more preferably 10 weight % or more, and even more preferably 20 weight % or more.

The dental adhesive according to the present invention exhibits excellent bond strength not only to tooth structures but also to crown restorative materials (such as metals, porcelains, ceramics, and cured composite materials) fractured in an oral cavity. In the case where the dental adhesive according to the present invention is used to bond a crown restorative material, the dental adhesive may be used in combination with a primer such as a commercially-available primer for metal bonding or porcelain bonding or in combination with a tooth cleaning agent such as a hypochlorite or a hydrogen peroxide solution.

These dental adhesives can be prepared and used according to conventional methods.

The present invention encompasses embodiments obtainable by combining the above components in various manners within the technical scope of the present invention as long as the effect of the present invention can be obtained.

EXAMPLES

Hereinafter, the present invention will be described in more detail by way of Examples. It should be noted that the present invention is not limited to Examples given below. Abbreviations used hereinafter are as follows.

[Asymmetric Acrylamide-Methacrylic Acid Ester Compound (a)]

MAEA: N-methacryloyloxyethyl acrylamide (asymmetric acrylamide-methacrylic acid ester compound represented by the following formula):

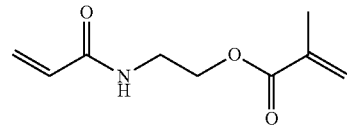

MAPA: N-methacryloyloxypropyl acrylamide (asymmetric acrylamide-methacrylic acid ester compound represented by the following formula):

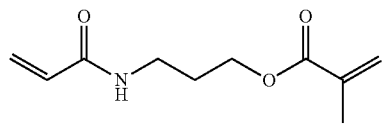

MAEEA: N-(1-ethyl-(2-methacryloyloxy)ethyl) acrylamide (asymmetric acrylamide-methacrylic acid ester compound represented by the following formula):

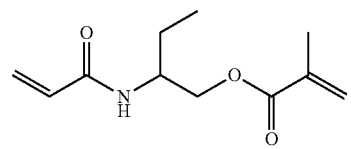

MAEGA: N-(2-(2-methacryloyloxyethoxy)ethyl) acrylamide (asymmetric acrylamide-methacrylic acid ester compound represented by the following formula):

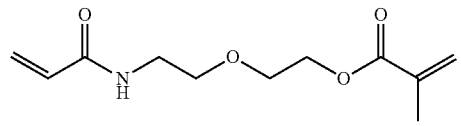 [SMILES: C=CC(=O)NCCOCCOC(=O)C(=C)C]

[Symmetric Methacrylamide-Methacrylic Acid Ester Compound]

MAEM: N-methacryloyloxyethyl acrylamide (symmetric methacrylamide-methacrylic acid ester compound represented by the following formula):

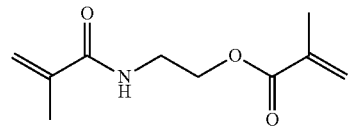

[Asymmetric (Meth)Acrylamide Compound]

NEBAE: N-ethyl-1,2-bis(acrylamide)ethane (asymmetric (meth)acrylamide compound represented by the following formula):

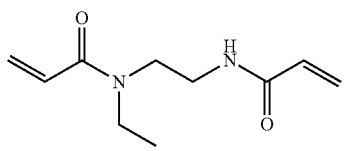

[Symmetric (Meth)Acrylamide Compound]
BAAE: Bisacrylamide ethylene (symmetric acrylamide compound represented by the following formula):

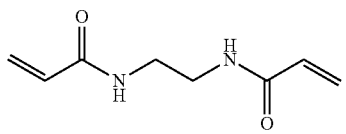

[Acid Group-Containing (Meth)Acrylic Polymerizable Monomer (b)]
MDP: 10-methacryloyloxydecyl dihydrogen phosphate
[Water-Soluble Polymerizable Monomer (c)]
DEAA: Diethyl acrylamide
HEMA: 2-hydroxyethyl methacrylate
GLM: 2,3-dihydroxypropyl methacrylate
[Hydrophobic Crosslinkable Polymerizable Monomer (d)]
Bis-GMA: 2,2-bis[4-(3-methacryloyloxy-2-hydroxypropoxy)phenyl]propane
UDMA: 2,2,4-trimethylhexamethylenebis(2-carbamoyloxyethyl) dimethacrylate
NPGDMA: Neopentyl glycol dimethacrylate
[Polymerization Initiator]
CQ: DL-camphorquinone
BAPO: Bis(2,4,6-trimethylbenzoyl)phenylphosphine oxide
[Polymerization Accelerator]
DABE: Ethyl 4-(N,N-dimethylamino)benzoate
DEPT: N,N-di(2-hydroxyethyl)-p-toluidine
[Filler]
R972: Silica fine particles "AEROSIL R972" manufactured by Nippon Aerosil Co., Ltd., having an average particle diameter of 16 nm
Ar380: Silica fine particles "AEROSIL Ar380" manufactured by Nippon Aerosil Co., Ltd., having an average particle diameter of 7 nm
[Others]
BHT: 2,6-di-t-butyl-4-methylphenol (stabilizer (polymerization inhibitor))

(Synthesis Example 1) Synthesis of MAEA 172.7 g (1.5 mol) of hydroxyethyl acrylamide (manufactured by Kohjin Film & Chemicals Co., Ltd.), 167 g (1.65 mol) of triethylamine, 38 mg (0.3 mmol) of p-methoxyphenol, and 1500 mL of anhydrous tetrahydrofuran were put into a 10-liter four-necked flask, stirred, and cooled to an internal temperature of −10° C. 700 mL of an anhydrous tetrahydrofuran solution of methacrylic acid chloride (172.5 g, 1.65 mol) was added dropwise at 5° C. or lower over 2 hours. After the dropwise addition of the solution, the resulting mixture was stirred for 24 hours under the conditions of room temperature. The resulting reaction solution was filtered, and insoluble matters were washed with ethyl acetate. The filtrate was concentrated under reduced pressure, and the residue was dissolved in ethyl acetate. The resulting solution was filtered with Celite to remove a small amount of insoluble matters, and then the filtrate was washed with a mixture of saturated saline solution and purified water (1:1). The organic layer was dried with anhydrous sodium sulfate, and then concentrated at 35° C. or lower under reduced pressure. The concentrated residue thus obtained was purified by silica gel column chromatography (developing solvent:ethyl acetate). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 201.2 g, and the percentage yield was 73.3%.
MS m/z: 184 (M+H)$^+$
$^1$H-NMR (270 MHz CDCl$_3$): δ 1.94 (m, 3H), 3.62 (m, 2H), 4.28 (m, 2H), 5.58 (m, 1H), 5.66 (m, 1H), 6.08 (s, 1H), 6.10 (m, 1H), 6.11 (m, 1H), 6.28 (m, 1H) (ppm)

(Synthesis Example 2) Synthesis of MAPA 23.9 g (0.318 mol) of 3-aminopropanol (manufactured by Tokyo Chemical Industry Co., Ltd.) and 400 mL of anhydrous tetrahydrofuran were put into a 1-liter four-necked flask, stirred, and cooled to an internal temperature of −10° C. 70 mL of an anhydrous tetrahydrofuran solution of acrylic acid chloride (14.4 g, 0.159 mol) was added dropwise at 5° C. or lower over 30 minutes. After the dropwise addition of the solution, the resulting mixture was stirred for 1 hour under the conditions of room temperature. After the reaction, insoluble matters were filtered and removed, and the filtrate was concentrated under reduced pressure. Thus, a pale yellow liquid was obtained.
12.9 g (0.1 mol) of hydroxypropyl acrylamide obtained by the procedure described above, 200 mL of anhydrous tetrahydrofuran, and 15.2 g (0.15 mol) of triethylamine were put into a 500-milliliter four-necked flask, stirred, and cooled to an internal temperature of −10° C. 50 mL of an anhydrous tetrahydrofuran solution of methacrylic acid chloride (15.7 g, 0.15 mol) was added dropwise at 5° C. or lower over 30 minutes. After the dropwise addition of the solution, the resulting mixture was stirred for 3 hours under the conditions of room temperature. After the reaction, triethylamine hydrochloride was filtered and removed, and the filtrate was concentrated under reduced pressure. The concentrated residue thus obtained was purified by silica gel column chromatography (developing solvent:ethyl acetate/hexane=2/1). After the column purification, the solvent was removed under reduced pressure using a rotary evaporator. Thus, a white solid was obtained. The solid was subjected to LC-MS analysis and $^1$H-NMR measurement. It was determined from the locations and integrals of signals that the white solid thus obtained was a target compound. The weight yield was 11.1 g, and the percentage yield was 56.3%.
MS m/z: 198 (M+H)$^+$
$^1$H-NMR (270 MHz CDCl$_3$): δ 1.93 (m, 2H), 1.97 (m, 3H), 3.42 (m, 2H), 4.27 (m, 2H), 5.58 (m, 1H), 5.65 (m, 1H), 6.11 (s, 1H), 6.10 (m, 1H), 6.13 (m, 1H), 6.30 (m, 1H) (ppm)

(Synthesis Example 3) Synthesis of MAEEA 28.3 g (0.318 mol) of DL-2-amino-1-butanol (manufactured by Tokyo Chemical Industry Co., Ltd.) and 400 mL of anhydrous tetrahydrofuran were put into a 1-liter four-necked flask, stirred, and cooled to an internal temperature of −10° C. 70 mL of an anhydrous tetrahydrofuran solution of acrylic acid chloride (14.4 g, 0.159 mol) was added dropwise at 5° C. or lower over 30 minutes. After the dropwise addition of the solution, the resulting mixture was stirred for 1 hour under the conditions of room temperature. After the reaction, insoluble matters were filtered and removed, and the filtrate was concentrated under reduced pressure. Thus, a pale yellow liquid was obtained.

14.3 g (0.1 mol) of N-(1-ethyl-(2-hydroxy)ethyl)acrylamide obtained by the procedure described above, 200 mL of anhydrous tetrahydrofuran, and 15.2 g (0.15 mol) of triethylamine were put into a 500-milliliter four-necked flask, stirred, and cooled to an internal temperature of −10° C. 50 mL of an anhydrous tetrahydrofuran solution of methacrylic acid chloride (15.7 g, 0.15 mol) was added dropwise at 5° C. or lower over 30 minutes. After the dropwise addition of the solution, the resulting mixture was stirred for 3 hours under the conditions of room temperature. After the reaction, triethylamine hydrochloride was filtered and removed, and the filtrate was concentrated under reduced pressure. The concentrated residue thus obtained was purified by silica gel column chromatography (developing solvent:ethyl acetate/hexane=2/1). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 7.7 g, and the percentage yield was 36.3%.

MS m/z: 212 (M+H)$^+$ $^1$H-NMR (270 MHz DMSO-d$_6$): δ 0.81 (m, 3H), 1.44 (m, 2H), 1.94 (m, 3H), 3.75 (m, 1H), 4.42 (m, 2H), 5.57 (m, 1H), 5.65 (m, 1H), 6.11 (m, 1H), 6.13 (m, 1H), 6.28 (m, 1H), 8.04 (s, 1H) (ppm)

(Synthesis Example 4) Synthesis of MAEGA 33.4 g (0.318 mol) of 2-(2-aminoethoxy)ethanol (manufactured by Tokyo Chemical Industry Co., Ltd.) and 400 mL of anhydrous tetrahydrofuran were put into a 1-liter four-necked flask, stirred, and cooled to an internal temperature of −10° C. 70 mL of an anhydrous tetrahydrofuran solution of acrylic acid chloride (14.4 g, 0.159 mol) was added dropwise at 5° C. or lower over 30 minutes. After the dropwise addition of the solution, the resulting mixture was stirred for 1 hour under the conditions of room temperature. After the reaction, insoluble matters were filtered and removed, and the filtrate was concentrated under reduced pressure. Thus, a pale yellow liquid was obtained.

15.9 g (0.1 mol) of N-(2-(2-hydroxyethoxy)ethyl)acrylamide obtained by the procedure described above, 200 mL of anhydrous tetrahydrofuran, and 15.2 g (0.15 mol) of triethylamine were put into a 500-milliliter four-necked flask, stirred, and cooled to an internal temperature of −10° C. 50 mL of an anhydrous tetrahydrofuran solution of methacrylic acid chloride (15.7 g, 0.15 mol) was added dropwise at 5° C. or lower over 30 minutes. After the dropwise addition of the solution, the resulting mixture was stirred for 3 hours under the conditions of room temperature. After the reaction, triethylamine hydrochloride was filtered and removed, and the filtrate was concentrated under reduced pressure. The concentrated residue thus obtained was purified by silica gel column chromatography (developing solvent:ethyl acetate/hexane=2/1). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 10.4 g, and the percentage yield was 45.8%.

MS m/z: 228 (M+H)$^+$ $^1$H-NMR (270 MHz DMSO-d$_6$): δ 1.93 (m, 3H), 3.28 (m, 2H), 3.43 (m, 2H), 3.49 (m, 2H), 4.34 (m, 2H), 5.59 (m, 1H), 5.63 (m, 1H), 6.09 (m, 1H), 6.12 (m, 1H), 6.30 (m, 1H), 8.17 (s, 1H) (ppm)

(Synthesis Example 5) Synthesis of NEBAE 200 g (2.269 mol) of N-ethylethylenediamine (manufactured by Koei Chemical Co., Ltd.), 688.9 g (6.807 mol) of trimethylamine, and 4 L of chloroform were put into a 10-liter four-necked flask, stirred, and cooled to an internal temperature of −10° C. 616.1 g (6.807 mol) of acrylic acid chloride was added dropwise at 10° C. or lower over 1 hour. After the dropwise addition of the solution, the resulting mixture was stirred for 1 hour under the conditions of room temperature. After the stirring was stopped, 4 L of water and 2 L of chloroform were added to the reaction solution for liquid-liquid extraction, and then the water layer was further extracted with 2 L of chloroform. The chloroform layer was washed with 4 L of water, dried with sodium sulfate, and then concentrated at 35° C. or lower under reduced pressure. The concentrated residue thus obtained was purified by silica gel column chromatography (developing solvent:ethyl acetate/methanol=10/1). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 127 g, and the percentage yield was 28.5%.

MS m/z: 197 (M+H)$^+$ $^1$H-NMR (270 MHz CDCl$_3$): δ 1.20 (m, 3H), 3.42 (m, 2H), 5.54 (m, 2H), 5.60 (m, 2H), 5.59 (m, 1H), 5.74 (m, 1H), 6.11 (m, 1H), 6.18 (m, 1H), 6.40 (m, 1H), 6.61 (m, 1H), 7.15 (s, 1H) (ppm)

(Synthesis Example 6) Synthesis of MAEM 19.4 g (0.318 mol) of 2-aminoethanol (manufactured by Tokyo Chemical Industry Co., Ltd.) and 400 mL of anhydrous tetrahydrofuran were put into a 1-liter four-necked flask, stirred, and cooled to an internal temperature of −10° C. 70 mL of an anhydrous tetrahydrofuran solution of methacrylic acid chloride (16.6 g, 0.159 mol) was added dropwise at 5° C. or lower over 30 minutes. After the dropwise addition of the solution, the resulting mixture was stirred for 3 hours under the conditions of room temperature. After the reaction, insoluble matters were filtered and removed, and the filtrate was concentrated under reduced pressure. Thus, a pale yellow liquid was obtained.

12.9 g (0.10 mol) of hydroxyethyl methacrylamide obtained by the procedure described above, 200 mL of anhydrous tetrahydrofuran, and 15.2 g (0.15 mol) of triethylamine were put into a 500-milliliter four-necked flask, stirred, and cooled to an internal temperature of −10° C. 50 mL of an anhydrous tetrahydrofuran solution of methacrylic acid chloride (15.7 g, 0.15 mol) was added dropwise at 5° C. or lower over 30 minutes. After the dropwise addition of the solution, the resulting mixture was stirred for 3 hours under the conditions of room temperature. After the reaction, triethylamine hydrochloride was filtered and removed, and the filtrate was concentrated under reduced pressure. The concentrated residue thus obtained was purified by silica gel column chromatography (developing solvent:ethyl acetate). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 10.8 g, and the percentage yield was 54.8%.

MS m/z: 198 (M+H)$^+$ $^1$H-NMR (270 MHz CDCl$_3$): δ 1.92 (m, 3H), 1.94 (m, 3H), 3.65 (m, 2H), 4.27 (m, 2H), 5.34 (m, 1H), 5.58 (m, 1H), 5.68 (m, 1H), 6.11 (m, 1H), 6.29 (s, 1H) (ppm)

BAAE

N,N'-ethylenebisacrylamide (manufactured by Alfa Aesar) was used.

Example 1 and Comparative Example 1

Application of Dental Adhesive to One-Step Adhesive System (One-Part Bonding Material)

One-part bonding materials having the compositions shown in Tables 1 and 2 were prepared using the materials given in the above-described synthesis examples and others. The unit of the values presented for the components listed in the tables is parts by weight. The details of specific Examples and Comparative Examples will be given hereinafter, followed by a description of the methods for their evaluation.

Examples 1-1 to 1-5

MAEA corresponding to the asymmetric acrylamide-methacrylic acid ester compound (a), MDP corresponding to the acid group-containing (meth)acrylic polymerizable monomer (b), DEAA corresponding to the water-soluble polymerizable monomer (c), and Bis-GMA corresponding to the hydrophobic crosslinkable polymerizable monomer (d) were used to obtain test specimens of one-part bonding materials according to the method for preparing specimens for the bond test described later. The bond strength and bond durability of these specimens were tested according to the bond strength test method and bond durability test method described later. In addition, the water absorption of the cured bonding materials and the mixed state of the components were tested according to the water absorption test method for cured bonding materials and the mixed state test method for components described later (it should be noted that in other examples and comparative examples, the bond strength and bond durability of the bonding materials, the water absorption of the cured bonding materials, and the mixed state of the components were tested according to the same test methods, respectively).

Examples 1-6 to 1-7

MAEA corresponding to the asymmetric acrylamide-methacrylic acid ester compound (a), MDP corresponding to the acid group-containing (meth)acrylic polymerizable monomer (b), DEAA and HEMA corresponding to the water-soluble polymerizable monomer (c), and Bis-GMA corresponding to the hydrophobic crosslinkable polymerizable monomer (d) were used to obtain one-part bonding materials. The bond strength and bond durability of the bonding materials, the water absorption of the cured bonding materials, and the mixed state of the components were tested.

Example 1-8

A one-part bonding material was prepared using the same materials as in Example 1-2 except that DEAA corresponding to the water-soluble polymerizable monomer (c) was changed as shown in Table 1. The bond strength and bond durability of the bonding material, the water absorption of the cured bonding material, and the mixed state of the components were tested.

Example 1-9

A one-part bonding material was prepared using the same materials as in Example 1-6 except that MAPA in an amount shown in Table 1 was used instead of MAEA corresponding to the asymmetric acrylamide-methacrylic acid ester compound (a). The bond strength and bond durability of the bonding material, the water absorption of the cured bonding material, and the mixed state of the components were tested.

Example 1-10

A one-part bonding material was prepared using the same materials as in Example 1-9 except that MAEEA was used instead of MAPA corresponding to the asymmetric acrylamide-methacrylic acid ester compound (a). The bond strength and bond durability of the bonding material, the water absorption of the cured bonding material, and the mixed state of the components were tested.

Example 1-11

A one-part bonding material was prepared using the same materials as in Example 1-9 except that MAEGA was used instead of MAPA corresponding to the asymmetric acrylamide-methacrylic acid ester compound (a). The bond strength and bond durability of the bonding material, the water absorption of the cured bonding material, and the mixed state of the components were tested.

Example 1-12

A one-part bonding material was prepared using the same materials as in Example 1-1 except that UDMA in an amount shown in Table 1 was used instead of Bis-GMA corresponding to the hydrophobic crosslinkable polymerizable monomer (d). The bond strength and bond durability of the bonding material, the water absorption of the cured bonding material, and the mixed state of the components were tested.

Example 1-13

A one-part bonding material was prepared using the same materials as in Example 1-2 except that acetone was used instead of ethanol corresponding to the organic solvent. The bond strength and bond durability of the bonding material, the water absorption of the cured bonding material, and the mixed state of the components were tested.

Example 1-14

A one-part bonding material was prepared using the same materials as in Example 1-2 except that NaF in an amount shown in Table 1 was used as a fluorine ion-releasing component. The bond strength and bond durability of the bonding material, the water absorption of the cured bonding material, and the mixed state of the components were tested.

Comparative Examples 1-1 to 1-2

MAEM corresponding to the symmetric methacrylamide-methacrylic acid ester compound, MDP corresponding to the acid group-containing (meth)acrylic polymerizable monomer (b), DEAA corresponding to the water-soluble polymerizable monomer (c), and Bis-GMA corresponding to the hydrophobic crosslinkable polymerizable monomer (d) were used to obtain one-part bonding materials. The bond strength and bond durability of the bonding materials, the water absorption of the cured bonding materials, and the mixed state of the components were tested.

Comparative Examples 1-3

NEBAE corresponding to the asymmetric acrylamide compound, MDP corresponding to the acid group-containing (meth)acrylic polymerizable monomer (b), and Bis-GMA corresponding to the hydrophobic crosslinkable polymerizable monomer (d) were used to obtain a one-part bonding material. The bond strength and bond durability of the bonding material, the water absorption of the cured bonding material, and the mixed state of the components were tested.

Comparative Examples 1-4

BAAE corresponding to the symmetric acrylamide compound, MDP corresponding to the acid group-containing (meth)acrylic polymerizable monomer (b), and Bis-GMA corresponding to the hydrophobic crosslinkable polymerizable monomer (d) were used to obtain a one-part bonding material. The bond strength and bond durability of the bonding material, the water absorption of the cured bonding material, and the mixed state of the components were tested.

[Bond Strength Test Method]

The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-μm-thick adhesive tape having a circular hole of 3-mm diameter, so that an adhesive area was defined.

The one-part bonding material prepared as described above was applied within the circular hole with a brush and left for 10 seconds, after which the applied one-part bonding material was dried by subjecting its surface to air-blowing until the bonding material lost its flowability. Subsequently, the applied one-part bonding material was cured by 10-second light irradiation with a dental visible light irradiation device (manufactured by Morita Corporation under the trade name "PenCure 2000").

To the surface of the obtained cured product of the one-part bonding material was applied a dental filling composite resin (manufactured by Kuraray Noritake Dental Inc. under the trade name "CLEARFIL AP-X" (registered trademark)), which was covered with a release film (made of polyester). Next, a glass slide was placed on and pressed against the release film to flatten the surface of the applied composite resin. Subsequently, the composite resin was cured by subjecting the resin to 20-second light irradiation through the release film using the irradiation device "PenCure 2000".

Using a commercially-available dental resin cement (manufactured by Kuraray Noritake Dental Inc. under the trade name "PANAVIA 21"), a cylindrical stainless steel rod (with a diameter of 7 mm and a length of 2.5 cm) was bonded at its one end face (circular end face) to the surface of the obtained cured product of the dental filling composite resin. Thus, a sample was obtained. After the bonding, the sample was allowed to stand at room temperature for 30 minutes, after which the sample was immersed in distilled water. A total of 16 enamel samples and a total of 16 dentin samples were prepared respectively for the bond test, and these samples were allowed to stand in a thermostat set at 37° C. for 24 hours. Immediately after the 24-hour standing, 8 of the 16 samples were subjected to measurement of their bond strength to evaluate the initial bond strength. The remaining 8 samples were subjected to 4000 cycles of a temperature cycling test, in which the cycle of alternately immersing the samples in 4° C. cold water for 1 minute and in 60° C. hot water for 1 minute was repeated, and then subjected to measurement of their bond strength to evaluate the bond durability.

The tensile bond strength of the above bond test samples was measured using a universal testing machine (manufactured by Shimadzu Corporation) with a crosshead speed set at 2 mm/minute. The average of the measured values of these samples was employed as the value of the tensile bond strength.

[Water Absorption Test]

Air was blown to the above-mentioned one-part bonding material until no weight change was observed, so as to remove water and the organic solvent. Thus, a sample for preparation of a cured product was obtained. The obtained sample was put in a Teflon (registered trademark) mold (with a diameter of 10 mm and a depth of 1 mm) placed on a glass slide covered with a polyester film. A polyester film was placed on the sample, and a glass sheet was further placed thereon and gently pressed against the polyester film. The sample was subjected to 10-second light irradiation with the above-mentioned irradiation device "PenCure 2000". Then, the sample was turned upside down and subjected to 10-second light irradiation in the same manner to cure the sample. Thus, a cured product of the one-part bonding material was obtained.

The surface of the obtained cured product was wiped to remove the unpolymerized portion, and the resulting cured product was immersed in water and then immersed in a thermostat set at 37° C. for 24 hours. The cured produced was removed from the thermostat and water was wiped off. Then, the weight (weight A) of the resulting cured product was measured. Subsequently, the cured product was dried in a thermostat set at 90° C. for 3 hours and cooled to room temperature in a dessicator containing silica gel. Then, the weight (weight B) of the resulting cured product was measured. The water absorption of the cured product was calculated by the following equation:

Water absorption (%)={(Weight $A$−Weight $B$)÷Weight $B$}×100

[Mixed State Test Method for Components of One-Part Bonding Material Composition]

The prepared one-part bonding material compositions were each placed in a glass bottle and visually observed from outside the bottle to determine whether the composition was cloudy or even partially phase-separated so as to evaluate the mixed state. The cloudy or even partially phase-separated compositions were determined to be "inhomogeneous" and the compositions with no cloudiness nor phase separation were determined to be "homogeneous", and the former was rated as "poor" and the latter was rated as "good".

TABLE 1

| Components (parts by weight) | | Example 1-1 | Example 1-2 | Example 1-3 | Example 1-4 | Example 1-5 | Example 1-6 | Example 1-7 |
|---|---|---|---|---|---|---|---|---|
| Asymmetric acrylamide-methacrylic acid ester compound (a) | MAEA | 20 | 15 | 5 | 3 | 10 | 20 | 27 |
| | MAPA | — | — | — | — | — | — | — |
| | MAEEA | — | — | — | — | — | — | — |
| | MAEGA | — | — | — | — | — | — | — |
| Acid group-containing (meth) acrylic monomer (b) | MDP | 10 | 10 | 10 | 10 | 10 | 10 | 10 |
| Water-soluble polymerizable monomer (c) | DEAA | 20 | 20 | 25 | 27 | 15 | 10 | 3 |
| | HEMA | — | — | — | — | — | 10 | 10 |
| | GLM | — | — | — | — | — | — | — |
| Hydrophobic polymerizable monomer (d) | Bis-GMA | 20 | 25 | 30 | 30 | 35 | 20 | 20 |
| | UDMA | — | — | — | — | — | — | — |
| Water | Distilled water | 15 | 15 | 15 | 15 | 15 | 15 | 15 |
| Organic solvent | Ethanol | 15 | 15 | 15 | 15 | 20 | 15 | 15 |
| | Acetone | — | — | — | — | — | — | — |
| Polymerization initiator | BAPO | 0.5 | 0.5 | 0.5 | 0.5 | 0.5 | 0.5 | 0.5 |
| | CQ | 2 | 2 | 2 | 2 | 2 | 2 | 2 |
| Polymerization accelerator | DABE | 1 | 1 | 1 | 1 | 1 | 1 | 1 |
| | DEPT | 0.5 | 0.5 | 0.5 | 0.5 | 0.5 | 0.5 | 0.5 |
| Polymerization inhibitor | BHT | 0.05 | 0.05 | 0.05 | 0.05 | 0.05 | 0.05 | 0.05 |
| Fluorine ion-releasing component | NaF | — | — | — | — | — | — | — |
| Filler | R972 | 7 | 7 | 7 | 7 | 7 | 7 | 7 |
| Bond strength test (MPa) | Enamel | 20 | 20 | 20 | 22 | 18 | 19 | 17 |
| | Dentin | 18 | 20 | 17 | 17 | 18 | 17 | 19 |
| Bond durability (MPa) | Enamel | 17 | 19 | 16 | 19 | 15 | 18 | 16 |
| | Dentin | 16 | 18 | 16 | 15 | 16 | 16 | 17 |
| Water absorption of cured bonding material (%) | | 3.1 | 2.9 | 3.6 | 3.8 | 3.3 | 3.6 | 3.4 |
| Mixed state of components | | Good | Good | Good | Good | Good | Good | Good |

| Components (parts by weight) | | Example 1-8 | Example 1-9 | Example 1-10 | Example 1-11 | Example 1-12 | Example 1-13 | Example 1-14 |
|---|---|---|---|---|---|---|---|---|
| Asymmetric acrylamide-methacrylic acid ester compound (a) | MAEA | 15 | — | — | — | 20 | 15 | 15 |
| | MAPA | — | 10 | — | — | — | — | — |
| | MAEEA | — | — | 10 | — | — | — | — |
| | MAEGA | — | — | — | 10 | — | — | — |
| Acid group-containing (meth) acrylic monomer (b) | MDP | 10 | 10 | 10 | 10 | 10 | 10 | 10 |
| Water-soluble polymerizable monomer (c) | DEAA | 10 | 10 | 10 | 10 | 15 | 20 | 20 |
| | HEMA | — | 10 | 10 | 10 | — | — | — |
| | GLM | 10 | — | — | — | — | — | — |
| Hydrophobic polymerizable monomer (d) | Bis-GMA | 25 | 20 | 20 | 20 | — | 25 | 25 |
| | UDMA | — | — | — | — | 25 | — | — |
| Water | Distilled water | 15 | 15 | 15 | 15 | 15 | 15 | 15 |
| Organic solvent | Ethanol | 15 | 15 | 15 | 15 | 15 | — | 15 |
| | Acetone | — | — | — | — | — | 15 | — |
| Polymerization initiator | BAPO | 0.5 | 0.5 | 0.5 | 0.5 | 0.5 | 0.5 | 0.5 |
| | CQ | 2 | 2 | 2 | 2 | 2 | 2 | 2 |
| Polymerization accelerator | DABE | 1 | 1 | 1 | 1 | 1 | 1 | 1 |
| | DEPT | 0.5 | 0.5 | 0.5 | 0.5 | 0.5 | 0.5 | 0.5 |
| Polymerization inhibitor | BHT | 0.05 | 0.05 | 0.05 | 0.05 | 0.05 | 0.05 | 0.05 |
| Fluorine ion-releasing component | NaF | — | — | — | — | — | — | 0.1 |

TABLE 1-continued

| Filler | R972 | 7 | 7 | 7 | 7 | 7 | 7 | 7 |
|---|---|---|---|---|---|---|---|---|
| Bond strength test (MPa) | Enamel | 21 | 19 | 18 | 20 | 20 | 19 | 20 |
| | Dentin | 21 | 18 | 19 | 19 | 17 | 18 | 19 |
| Bond durability (MPa) | Enamel | 18 | 17 | 16 | 16 | 17 | 16 | 18 |
| | Dentin | 20 | 16 | 17 | 15 | 16 | 16 | 18 |
| Water absorption of cured bonding material (%) | | 4.0 | 3.8 | 4.4 | 3.7 | 3.0 | 3.1 | |
| Mixed state of components | | Good | Good | Good | Good | Good | Good | |

TABLE 2

| Components (parts by weight) | | Comparative Example 1-1 | Comparative Example 1-2 | Comparative Example 1-3 | Comparative Example 1-4 |
|---|---|---|---|---|---|
| Symmetric methacrylamide-methacrylic acid ester compound | MAEM | 25 | 15 | — | — |
| Asymmetric acrylamide compound | NEBAE | — | — | 30 | — |
| Symmetric acrylamide compound | BAAE | — | — | — | 30 |
| Acid group-containing (meth)acrylic monomer (b) | MDP | 10 | 10 | 10 | 10 |
| Water-soluble polymerizable monomer (c) | DEAA | 5 | 15 | — | — |
| Hydrophobic polymerizable monomer (d) | Bis-GMA | 30 | 30 | 30 | 30 |
| Water | Distilled water | 15 | 15 | 15 | 15 |
| Organic solvent | Ethanol | 15 | 15 | 15 | 15 |
| Polymerization initiator | BAPO | 0.5 | 0.5 | 0.5 | 0.5 |
| | CQ | 9 | 9 | 9 | 9 |
| Polymerization accelerator | DABE | 1 | 1 | 1 | 1 |
| | DEPT | 0.5 | 0.5 | 0.5 | 0.5 |
| Polymerization inhibitor | BHT | 0.05 | 0.05 | 0.05 | 0.05 |
| Filler | R972 | 7 | 7 | 7 | 7 |
| Bond strength test (MPa) | Enamel | 16 | 18 | 17 | 9 |
| | Dentin | 14 | 15 | 18 | 10 |
| Bond durability (MPa) | Enamel | 13 | 13 | 13 | 7 |
| | Dentin | 9 | 11 | 12 | 6 |
| Water absorption of cured bonding material (%) | | 5.2 | 5.4 | 5.8 | NA |
| Mixed state of components | | Good | Good | Good | Poor |

As shown in Table 1, the one-part bonging materials (Examples 1-1 to 1-14) as examples of the dental adhesive according to the present invention exhibited a bond strength of 15 MPa or more and a bond durability of 15 MPa or more to both enamel and dentin. Table 1 shows that the one-part bonding materials as examples of the dental adhesive according to the present invention had a water absorption of 4.4% or less when they were cured, which means that these bonding materials had very high homogeneity. On the other hand, Table 2 shows that the one-part bonding materials (Comparative Examples 1-1 and 1-2) not containing the asymmetric acrylamide-methacrylic acid ester compound (a) of the present invention but instead containing a symmetric methacrylamide-methacrylic acid ester compound MAEM having two polymerizable groups, one of which is a methacrylic acid ester group and the other of which is a methacrylamide group as a secondary amide group, had a bond durability of 13 MPa or less to both enamel and dentin and a water absorption of more than 5%. The bonding material (Comparative Example 1-3) containing an asymmetric acrylamide compound NEBAE instead of the asymmetric acrylamide-methacrylic acid ester compound (a) had a water absorption of more than 5% when it was cured and had a bond durability of 13 MPa or less to both enamel and dentin. Furthermore, the bonding material (Comparative Example 1-4) containing a symmetric acrylamide compound BAAE instead of the asymmetric acrylamide-methacrylic acid ester compound (a) had poor compatibility with other components and the resulting composition was inhomogeneous. In addition, this bonding material had a bond strength of 10 MPa or less and a bond durability of 10 MPa or less to both enamel and dentin. In particular, the bond durability was 7 MPa or less to both enamel and dentin.

Example 2 and Comparative Example 2

Application of Dental Adhesive to Two-Step Adhesive System (Primer)

Primers having the compositions shown in Table 3 were prepared using the materials given in the above-described synthesis examples and others. Bonding materials having the compositions shown in Table 4 were also prepared. The unit of the values presented for the components listed in the tables is parts by weight. The details of specific Examples and Comparative Examples will be given hereinafter, followed by a description of the methods for their evaluation.

Example 2-1

MAEA corresponding to the asymmetric acrylamide-methacrylic acid ester compound (a), MDP corresponding to the acid group-containing (meth)acrylic polymerizable monomer (b), and DEAA corresponding to the water-soluble polymerizable monomer (c) were used to obtain a test specimen of a primer according to the method for preparing specimens for the bond test described later. The bond strength and bond durability of the specimen were tested according to the bond strength test method and bond durability test method described later. The mixed state of the components was also tested (it should be noted that in other examples and comparative examples, the bond strength, the bond durability, and the mixed state of the components were tested according to the same test methods, respectively).

Example 2-2

MAEA corresponding to the asymmetric acrylamide-methacrylic acid ester compound (a), MDP corresponding to the acid group-containing (meth)acrylic polymerizable monomer (b), and DEAA and HEMA corresponding to the water-soluble polymerizable monomer (c) were used to obtain a primer. The bond strength and bond durability of the primer and the mixed state of the components were tested.

Example 2-3

A primer was prepared using the same materials as in Example 2-1 except that MAPA was used instead of MAEA corresponding to the asymmetric acrylamide-methacrylic acid ester compound (a) and a combination of DEAA and HEMA was used instead of DEAA alone corresponding to the water-soluble polymerizable monomer (c). The bond strength and bond durability of the primer and the mixed state of the components were tested.

Example 2-4

A primer was prepared using the same materials as in Example 2-3 except that MAEEA was used instead of MAPA corresponding to the asymmetric acrylamide-methacrylic acid ester compound (a). The bond strength and bond durability of the primer and the mixed state of the components were tested.

Example 2-5

A primer was prepared using the same materials as in Example 2-3 except that MAEGA was used instead of MAPA corresponding to the asymmetric acrylamide-methacrylic acid ester compound (a). The bond strength and bond durability of the primer and the mixed state of the components were tested.

Comparative Example 2-1

A primer was prepared using MAEM corresponding to the symmetric methacrylamide-methacrylic acid ester compound. The bond strength and bond durability of the primer and the mixed state of the components were tested.

Comparative Example 2-1

A primer was prepared using BAAE corresponding to a symmetric acrylamide compound and MDP corresponding to the acid group-containing (meth)acrylic polymerizable monomer (b). The bond strength and bond durability of the primer and the mixed state of the components were tested.

[Bond Strength Test Method]

The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-μm-thick adhesive tape having a circular hole of 3-mm diameter, so that an adhesive area was defined.

The primer prepared as described above was applied within the circular hole with a brush and left for 20 seconds, after which the applied primer was dried by subjecting its surface to air-blowing until the primer lost its flowability. Next, the bonding material having the composition shown in Table 4 was applied over the primer applied and dried on the tooth surface. Subsequently, the applied primer and bonding material were cured by 10-second light irradiation with a dental visible light irradiation device (manufactured by Morita Corporation under the trade name "PenCure 2000").

To the surface of the obtained cured product of the bonding material was applied a dental filling composite resin (manufactured by Kuraray Noritake Dental Inc. under the trade name "CLEARFIL AP-X" (registered trademark)), which was covered with a release film (made of polyester). Next, a glass slide was placed on and pressed against the release film to flatten the surface of the applied composite resin. Subsequently, the composite resin was cured by subjecting the resin to 20-second light irradiation through the release film using the irradiation device "PenCure 2000".

Using a commercially-available dental resin cement (manufactured by Kuraray Noritake Dental Inc. under the trade name "PANAVIA 21"), a cylindrical stainless steel rod (with a diameter of 7 mm and a length of 2.5 cm) was bonded at its one end face (circular end face) to the surface of the obtained cured product of the dental filling composite resin. Thus, a sample was obtained. After the bonding, the sample was allowed to stand at room temperature for 30 minutes, after which the sample was immersed in distilled water. A total of 16 enamel samples and a total of 16 dentin samples were prepared respectively for the bond test, and these samples were allowed to stand in a thermostat set at 37° C. for 24 hours. Immediately after the 24-hour standing, 8 of the 16 samples were subjected to measurement of their bond strength to evaluate the initial bond strength. The remaining 8 samples were subjected to 4000 cycles of a temperature cycling test, in which the cycle of alternately immersing the samples in 4° C. cold water for 1 minute and in 60° C. hot water for 1 minute was repeated, and then subjected to measurement of their bond strength to evaluate the bond durability.

The tensile bond strength of the above bond test samples was measured using a universal testing machine (manufactured by Shimadzu Corporation) with a crosshead speed set at 2 mm/minute. The average of the measured values of these samples was employed as the value of the tensile bond strength.

[Mixed State Test Method for Components of Primer Composition]

The prepared primer compositions were each placed in a glass bottle and visually observed from outside the bottle to determine whether the composition was cloudy or even partially phase-separated so as to evaluate the mixed state. The cloudy or even partially phase-separated compositions were determined to be "inhomogeneous" and the compositions with no cloudiness nor phase separation were determined to be "homogeneous", and the former was rated as "poor" and the latter was rated as "good".

TABLE 3

| Components (parts by weight) | | Example 2-1 | Example 2-2 | Example 2-3 | Example 2-4 | Example 2-5 | Com. Ex- ample 2-1 | Com. Ex- ample 2-1 |
|---|---|---|---|---|---|---|---|---|
| Asymmetric acrylamide- methacrylic acid ester compound (a) | MAEA | 10 | 20 | — | — | — | — | — |
| | MAPA | — | — | 10 | — | — | — | — |
| | MAEEA | — | — | — | 10 | — | — | — |
| | MAEGA | — | — | — | — | 10 | — | — |
| Symmetric acrylamide- methacrylic acid ester compound | MAEM | — | — | — | — | — | 33 | — |
| Symmetric acrylamide compound | BAAE | — | — | — | — | — | — | 40 |
| Acid group- containing (meth)acrylic monomer (b) | MDP | 15 | 15 | 15 | 15 | 15 | — | 15 |
| Water-soluble polymerizable monomer (c) | DEAA | 30 | 5 | 15 | 15 | 15 | — | — |
| | HEMA | — | 15 | 15 | 15 | 15 | — | — |
| Water | Distilled water | 40 | 40 | 40 | 40 | 40 | 34 | 40 |
| Polymerization initiator | BAPO | 0.1 | 0.1 | 0.1 | 0.1 | 0.1 | — | 0.1 |
| | CQ | 0.2 | 0.2 | 0.2 | 0.2 | 0.2 | 0.102 | 0.2 |
| Polymerization accelerator | DABE | 0.1 | 0.1 | 0.1 | 0.1 | 0.1 | — | 0.1 |
| | DEPT | 3 | 3 | 3 | 3 | 3 | — | 3 |
| Polymerization inhibitor | BHT | 0.05 | 0.05 | 0.05 | 0.05 | 0.05 | — | 0.05 |
| Bond strength test (MPa) | Enamel | 17 | 18 | 17 | 18 | 19 | 0 | 7 |
| | Dentin | 20 | 20 | 19 | 18 | 18 | 0 | 10 |
| Bond durability (MPa) | Enamel | 16 | 17 | 16 | 16 | 16 | 0 | 5 |
| | Dentin | 18 | 18 | 17 | 16 | 15 | 0 | 7 |
| Mixed state of components | | Good | Good | Good | Good | Good | Good | Poor |

TABLE 4

| Components | Content (parts by weight) |
|---|---|
| Bis-GMA | 40 |
| HEMA | 40 |
| NPGDMA | 20 |
| CQ | 0.6 |
| BAPO | 0.5 |
| DABE | 2 |
| R972 | 6 |
| Ar380 | 1.5 |

As shown in Table 3, the primers (Examples 2-1 to 2-5) as examples of the dental adhesive according to the present invention exhibited a bond strength of 15 MPa or more and a bond durability of 15 MPa or more to both enamel and dentin. Table 3 shows that the primers as examples of the dental adhesive according to the present invention had very high homogeneity. On the other hand, Table 3 shows that the primer (Comparative Example 2-1) not containing the asymmetric acrylamide-methacrylic acid ester compound (a) of the present invention but instead containing a symmetric methacrylamide-methacrylic acid ester compound MAEM having two polymerizable groups, one of which is a methacrylic acid ester group and the other of which is a methacrylamide group as a secondary amide group, had no adhesiveness to both enamel and dentin. Furthermore, the primer (Comparative Example 2-2) containing a symmetric acrylamide compound BAAE instead of the asymmetric acrylamide-methacrylic acid ester compound (a) had poor compatibility with other components and the resulting composition was inhomogeneous. In addition, this primer had a bond strength of 10 MPa or less and a bond durability of 10 MPa or less to both enamel and dentin. In particular, the bond durability was 7 MPa or less to both enamel and dentin.

INDUSTRIAL APPLICABILITY

The dental adhesive according to the present invention can be used in various dental adhesive materials such as a primer and a bonding material, and can be particularly suitably used as a one-part bonding material.

The invention claimed is:
1. A dental adhesive comprising:
an asymmetric acrylamide-methacrylic acid ester compound (a);
an acid group-containing (meth)acrylic polymerizable monomer (b); and
a water-soluble polymerizable monomer (c), wherein
the asymmetric acrylamide-methacrylic acid ester compound (a) is represented by formula (1):

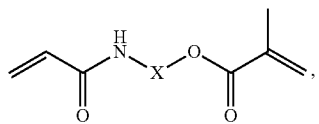

(1)

wherein X is an optionally substituted, linear or branched $C_1$ to $C_6$ aliphatic group or an optionally substituted aromatic group, the aliphatic group is optionally interrupted by at least one linking group selected from the group consisting of —O—, —S—, —CO—, —O—CO—, —NR$^1$—, —CO—NR$^1$—, —NR$^1$—CO—, —CO—O—NR$^1$—, —O—CO—NR$^1$—, and —NR$^1$—CO—NR$^1$—, and R$^1$ is a hydrogen atom or an optionally substituted, linear or branched $C_1$ to $C_6$ aliphatic group.

2. The dental adhesive according to claim 1, wherein X is an optionally substituted, linear or branched $C_1$ to $C_4$ aliphatic group.

3. The dental adhesive according to claim 1, wherein X is an optionally substituted, linear or branched $C_2$ to $C_4$ aliphatic group, and R$^1$ is a hydrogen atom.

4. The dental adhesive according to claim 1, further comprising a hydrophobic crosslinkable polymerizable monomer (d).

5. The dental adhesive according to claim 1, wherein the acid group-containing (meth)acrylic polymerizable monomer (b) is a phosphate group-containing (meth)acrylic polymerizable monomer.

6. The dental adhesive according to claim 1, wherein the water-soluble polymerizable monomer (c) comprises at least one selected from the group consisting of a monofunctional (meth)acrylamide compound (c-1), 2-hydroxyethyl (meth)acrylate, 2,3-dihydroxypropyl (meth)acrylate, and diacetone (meth)acrylamide, the monofunctional (meth)acrylamide compound (c-1) being represented by formula (2):

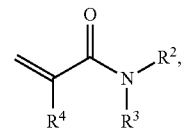

(2)

wherein R$^2$ and R$^3$ are each independently an optionally substituted, linear or branched $C_1$ to $C_3$ alkyl group, and R$^4$ is a hydrogen atom or a methyl group.

7. The dental adhesive according to claim 1, wherein the water-soluble polymerizable monomer (c) is a monofunctional (meth)acrylamide compound (c-1) represented by formula (2):

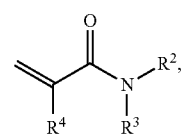

(2)

wherein R$^2$ and R$^3$ are each independently an optionally substituted, linear or branched $C_1$ to $C_3$ alkyl group, and R$^4$ is a hydrogen atom or a methyl group.

8. The dental adhesive according to claim 1, wherein a weight ratio between the water-soluble polymerizable monomer (c) and the asymmetric acrylamide-methacrylic acid ester compound (a) is 10:1 to 1:10.

* * * * *